United States Patent
Harlev et al.

(10) Patent No.: US 8,433,394 B2
(45) Date of Patent: *Apr. 30, 2013

(54) CARDIAC MAPPING

(75) Inventors: Doron Harlev, Cambridge, MA (US); Pavel Greenfield, Havertown, PA (US); Leon Amariglio, Somerville, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 13/044,937

(22) Filed: Mar. 10, 2011

(65) Prior Publication Data
US 2011/0190625 A1 Aug. 4, 2011

Related U.S. Application Data

(63) Continuation of application No. 12/138,678, filed on Jun. 13, 2008, now Pat. No. 7,957,791, which is a continuation of application No. 11/451,898, filed on Jun. 13, 2006, now Pat. No. 7,515,954.

(51) Int. Cl.
A61B 5/02 (2006.01)
(52) U.S. Cl.
USPC .......................................... 600/509
(58) Field of Classification Search .................. 600/509, 600/512
See application file for complete search history.

(56) References Cited

U.S. PATENT DOCUMENTS

| 4,649,924 A | 3/1987 | Taccardi |
| 4,674,518 A | 6/1987 | Salo ............................ 128/695 |
| 4,840,182 A | 6/1989 | Carlson ......................... 128/694 |
| 4,920,490 A | 4/1990 | Isaacson .................. 364/413.13 |
| 5,156,151 A | 10/1992 | Imran |
| 5,284,142 A | 2/1994 | Goble et al. ............... 128/653.1 |
| 5,297,549 A | 3/1994 | Beatty et al. |
| 5,300,068 A | 4/1994 | Rosar et al. ..................... 606/34 |
| 5,341,807 A | 8/1994 | Nardella |
| 5,381,333 A | 1/1995 | Isaacson et al. ......... 364/413.13 |
| 5,469,858 A | 11/1995 | Osborne |
| 5,480,422 A | 1/1996 | Ben-Haim |
| 5,500,011 A | 3/1996 | Desai |
| 5,553,611 A | 9/1996 | Budd et al. .................... 128/642 |
| 5,568,809 A | 10/1996 | Ben-Haim |

(Continued)

FOREIGN PATENT DOCUMENTS

| JP | 2001-292973 | 10/2001 |
| JP | 2002-51998 | 2/2002 |
| WO | 99/06112 | 2/1999 |

OTHER PUBLICATIONS

Authorized officer Michael Becker, Communication pursuant to Article 94(3) EPC in European Application No. 07 798 369.0 mailed Nov. 17, 2011, 5 pages.

(Continued)

Primary Examiner — Brian T Gedeon
(74) Attorney, Agent, or Firm — Fish & Richardson P.C.

(57) ABSTRACT

A non-contact cardiac mapping method is disclosed that includes: (i) inserting a catheter into a heart cavity having an endocardium surface, the catheter including multiple, spatially distributed electrodes; (ii) measuring signals at the catheter electrodes in response to electrical activity in the heart cavity with the catheter spaced from the endocardium surface; and (iii) determining physiological information at multiple locations of the endocardium surface based on the measured signals and positions of the electrodes with respect to the endocardium surface. Related systems and computer programs are also disclosed.

33 Claims, 13 Drawing Sheets

U.S. PATENT DOCUMENTS

| | | | |
|---|---|---|---|
| 5,577,502 A | 11/1996 | Darrow et al. | 128/653.1 |
| 5,588,429 A | 12/1996 | Isaacson et al. | |
| 5,662,108 A | 9/1997 | Budd et al. | |
| 5,687,737 A | 11/1997 | Branham et al. | |
| 5,697,377 A | 12/1997 | Wittkampf | |
| 5,704,365 A | 1/1998 | Albrecht et al. | |
| 5,722,402 A | 3/1998 | Swanson et al. | 128/642 |
| 5,840,025 A | 11/1998 | Ben-Haim | |
| 5,840,031 A | 11/1998 | Crowley | |
| 5,846,198 A | 12/1998 | Killmann | 600/424 |
| 5,848,972 A | 12/1998 | Triedman et al. | |
| 5,921,982 A | 7/1999 | Lesh et al. | 606/41 |
| 5,954,665 A | 9/1999 | Ben-Haim | |
| 5,971,933 A | 10/1999 | Gopakumaran et al. | 600/526 |
| 5,983,126 A | 11/1999 | Wittkampf | |
| 6,050,267 A | 4/2000 | Nardella et al. | |
| 6,095,150 A | 8/2000 | Panescu et al. | 128/899 |
| 6,167,296 A | 12/2000 | Shahidi | |
| 6,226,542 B1 | 5/2001 | Reisfeld | |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | 600/407 |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | 600/410 |
| 6,318,375 B1 | 11/2001 | Plicchi et al. | 128/899 |
| 6,360,123 B1 | 3/2002 | Kimchi et al. | 600/547 |
| 6,368,285 B1 | 4/2002 | Osadchy et al. | 600/508 |
| 6,400,981 B1 | 6/2002 | Govari | |
| 6,516,807 B1 | 2/2003 | Panescu et al. | |
| 6,547,082 B1 | 4/2003 | Babini | 211/41.17 |
| 6,556,695 B1 | 4/2003 | Packer et al. | |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | |
| 6,600,948 B2 | 7/2003 | Ben-Haim et al. | |
| 6,603,996 B1 | 8/2003 | Beatty et al. | |
| 6,631,290 B1 | 10/2003 | Guck et al. | |
| 6,640,119 B1 | 10/2003 | Budd et al. | 600/374 |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | 600/420 |
| 6,839,588 B1 | 1/2005 | Rudy | |
| 6,847,839 B2 | 1/2005 | Ciaccio et al. | |
| 6,872,428 B2 | 3/2005 | Yang et al. | 427/568 |
| 6,892,090 B2 | 5/2005 | Verard et al. | 600/424 |
| 6,892,091 B1 | 5/2005 | Ben-Haim et al. | 600/509 |
| 6,939,309 B1 | 9/2005 | Beatty et al. | 600/508 |
| 6,957,101 B2 | 10/2005 | Porath et al. | |
| 6,978,168 B2 | 12/2005 | Beatty et al. | |
| 6,990,370 B1 | 1/2006 | Beatty et al. | 600/509 |
| 7,016,719 B2 | 3/2006 | Rudy et al. | |
| 7,043,292 B2 | 5/2006 | Tarjan et al. | |
| 7,263,397 B2 | 8/2007 | Hauck et al. | 600/374 |
| 7,505,810 B2 | 3/2009 | Harlev et al. | |
| 7,515,954 B2 | 4/2009 | Harlev et al. | |
| 7,729,752 B2 | 6/2010 | Harlev et al. | |
| 2002/0151807 A1 | 10/2002 | Goldin | |
| 2003/0018251 A1 | 1/2003 | Solomon | |
| 2003/0065271 A1 | 4/2003 | Khoury | |
| 2003/0076277 A1 | 4/2003 | Muramatsu et al. | 345/1.1 |
| 2003/0216630 A1 | 11/2003 | Jersey-Willuhn et al. | |
| 2004/0077942 A1 | 4/2004 | Hall et al. | 600/428 |
| 2004/0097806 A1 | 5/2004 | Hunter et al. | |
| 2004/0243015 A1 | 12/2004 | Smith et al. | |
| 2004/0254437 A1 | 12/2004 | Hauck et al. | |
| 2005/0038337 A1 | 2/2005 | Edwards | 600/424 |
| 2005/0054918 A1 | 3/2005 | Sra | |
| 2005/0107834 A1 | 5/2005 | Freeman et al. | |
| 2005/0154282 A1 | 7/2005 | Li et al. | 600/407 |
| 2005/0288599 A1 | 12/2005 | MacAdam et al. | 600/509 |
| 2006/0085049 A1 | 4/2006 | Cory et al. | 607/48 |
| 2006/0116575 A1 | 6/2006 | Willis | |
| 2006/0122526 A1 | 6/2006 | Berenfeld et al. | |
| 2006/0173251 A1 | 8/2006 | Govari et al. | 600/306 |
| 2006/0178587 A1 | 8/2006 | Khoury | |
| 2006/0241401 A1 | 10/2006 | Govari et al. | 600/424 |
| 2007/0016007 A1 | 1/2007 | Govari et al. | 600/424 |
| 2007/0038078 A1 | 2/2007 | Osadchy | 600/424 |
| 2007/0049821 A1 | 3/2007 | Willis | |
| 2007/0197929 A1 | 8/2007 | Porath et al. | |
| 2007/0265539 A1 | 11/2007 | Hastings et al. | |
| 2007/0287902 A1 | 12/2007 | Fuimaono et al. | |
| 2007/0299351 A1 | 12/2007 | Harlev et al. | 600/509 |
| 2007/0299352 A1 | 12/2007 | Harlev et al. | |
| 2008/0190438 A1 | 8/2008 | Harlev et al. | |
| 2008/0221566 A1 | 9/2008 | Krishnan | |
| 2008/0234588 A1 | 9/2008 | Feldman et al. | |
| 2008/0249424 A1 | 10/2008 | Harlev et al. | |
| 2009/0171274 A1 | 7/2009 | Harlev et al. | |
| 2009/0177072 A1 | 7/2009 | Harlev et al. | |
| 2009/0253976 A1 | 10/2009 | Harlev et al. | |
| 2010/0286551 A1 | 11/2010 | Harlev et al. | |

OTHER PUBLICATIONS

Arthur, "Clinical Use of Intracardiac Impedance: Current Applications and Future Perspectives", PACE, vol. 24:500-506, Apr. 2001.

Authorized officer Johan Bengisson, Communication pursuant to Article 94(3) EPC in European Application No. 07 798 369.0 mailed Nov. 17, 2011, 5 pages (0002EPI).

Authorized office Yoshiko Kuwahara, International Preliminary Report on Patentability in PCT/US2007/070854, mailed Dec. 31, 2008, 10 pages (0002WOI).

Badies, "Real-Time Reconstruction of Endocardial Potential Maps in Non-Contact Cardiac Mapping", International Journal for computation and Mathematics in Electrical Engineering (COMPEL), vol. 28, No. 4, 2009.

Cheney et al., "Electrical Impedance Tomography", SIAM Review 41:85-101, 1999.

E. J. Haug, K. K. Choi, V. Komkov: Design Sensitivity Analysis of Structural Systems, Mathematics in Science and Engineering, vol. 177 (1986).

Kuklik et al., "The reconstruction, from a set of points, and analysis of the interior surface of the heart chamber", Physiol. Meas. 25:617-627, 2004.

L. Piegl, W. Tiller: The NURBS Book, 2nd Edition, Springer (1997).

Notice of Reasons for Rejection in JP Application No. 2009-515586, mailed Jun. 26, 2012, 8 pages (0002JPI).

Adams et al., "Seeded Region Growing", *IEEE Transactions on Pattern Analysis and Machine Intelligence*, 16(6):641-647, 1994.

Authorized examiner Johan Bengtsson, Supplementary European Search Report in Application No. 07798369.0 mailed Jul. 30, 2010, 6 pages.

Authorized officer Brian T. Gedeon, Notice of Allowance in U.S. Appl. No. 11/451,898 dated Jan. 29, 2009 (9 pages).

Authorized officer Brian T. Gedeon, Office Action in U.S. Appl. No. 11/451,898 dated Sep. 25, 2008 (20 pages).

Authorized officer Brian T. Gedeon, Notice of Allowance in U.S. Appl. No. 12/138,678 dated Feb. 1, 2011 (23 pages).

Baan, Jan et al., "Continuous Measurement of Left Ventricular Volume in Animals and Humans by Conductance Catheter", Circulation, vol. 70,pp. 812-823, Dec. 1984.

Ben-Haim et al., "Nonfluoroscopic, in Vivo Navigation and Mapping Technology", Nature Medicine, 2(12):1393-1395, 1996.

Besl et al., "A Method for Registration of 3-D Shapes", *IEEE Transactions on Pattern Analysis and Machine Intelligence*, 14(2):239-256, 1992.

Blomström-Lundqvist et al., "ACC/AHA/ESC Guidelines for the Management of Patients With Supraventricular Arrhythmias-Executive Summary", *Journal of the American College of Cardiology*, 42(8):1493-1531, 2003.

Breithardt et al., "AHA Medical/Scientific Statement—Special Report: Standards for Analysis of Ventricular Late Potentials Using High-Resolution or Signal-Averaged Electrocardiography", *Circulation*, 83(4):1481-1488, 1991.

Brooks et al., "Electrical Imaging of the Heart", *IEEE Signal Processing Magazine*, pp. 24-42, 1997.
Caspi et al., "Stem Cell Research: Regenerating the Heart Using Human Embryonic Stem Cells—from Cell to Bedside", *IMAJ*, 8:208-214, 2006.
De Groot et al., "Three-Dimensional Catheter Positioning During Radiofrequency Ablation in Patients: First Application of a Real-Time Position Management System", *Journal of Cardiovascular Electrophysiology*, 11:1183-1192, 2000.
Donahue et al., "Focal Modification of Electrical Conduction in the Heart by Viral Gene Transfer", *Nature Medicine*, 6(12):1395-1398, 2000.
Dong et al., "Integrated Electroanatomic Mapping With Three-Dimensional Computed Tomographic Images for Real-Time Guided Ablations", *Circulation*, 113:186-194, 2006.
Durrer et al., "Total Excitation of the Isolated Human Heart", *Circulation*, vol. XLI, pp. 899-912, 1970.
Ector, Joris et al., "Cardiac Three-Dimensional Magnetic Resonance Imaging and Fluoroscopy Merging", Circulation, (Dec. 13, 2005).
Fish & Richardson, Response to Office Action in U.S. Appl. No. 11/451,898, filed Nov. 4, 2008 (25 pages).
Friedman, "Catheter Cryoablation of Cardiac Arrhythmias", *Current Opinion in Cardiology*, 20:48-54, 2005.
Friedman, "Novel Mapping Techniques for Cardiac Electrophysiology", *Heart*, 87:575-582, 2002.
Geddes, L.A. et al., "Criteria for the Selection of Materials for Implanted Electrodes", Annals of Biomedical Engineering, vol. 31, pp. 879-890 (2003).
Gepstein et al., "A Novel Method for Nonfluoroscopic Catheter-Based Electroanatomical Mapping of the Heart", *Circulation* 95:1611-1622, 1997.
Huang, Yi-Chih et al., "Development of a Third Generation Intraventricular Impedance Imaging (Iii) System Evaluation of Hardware Design", Engineering in Medicine and Biology Society,. Proceedings of the 19th Annual International Conference of the IEEE, Oct. 30-Nov. 2, 1997 vol. 6, (1997).
International Search Report and he Written Opinion, PCT/US08/52385, Aug. 8, 2008, 11 pages.
Jain et al., "Cell Therapy Attenuates Deleterious Ventricular Remodeling and Improves Cardiac Performance After Myocardial Infarction", *Circulation*, 103:1920-1927, 2001.
Jalife, "Rotors and Spiral Waves in Atrial Fibrillation", *Journal of Cardiovascular Electrophysiology*, 14:776-780, 2003.
Jané et al., "Alignment Methods for Averaging of High-Resolution Cardiac Signals: A Comparative Study of Performance", *IEEE Transactions on Biomedical Engineering*, 38(6):571-579, 1991.
Jia et al., "Electrophysiologic Endocardial Mapping From a Noncontact Nonexpandable Catheter: A Validation Study of a Geometry-Based Concept", *Journal of Cardiovascular Electrophysiology*, 11:1238-1251, 2000.
Kikuchi et al., "Targeted Modification of Atrial Electrophysiology by Homogeneous Transmural Atrial Gene Transfer", *Circulation*, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", *Journal of Cardiovascular Electrophysiology*, 17:341-348, 2006.
Kun, Stevan et al., "Conductance Volumetric Model of an Eccentrically Positioned Catheter Within A Three-Compartment Ellipsoidal Ventricle", U, IEEE Transactions on, Jun. 1993, vol. 40, Issue: 6.
Laciar et al., "Improved Alignment Method for Noisy High-Resolution ECG and Holter Records Using Multistate Cross-Correlation", *IEEE Transactions on Biomedical Engineering*, 50(3):344-353, 2003.
Liu et al., "Endocardial Potential Mapping From a Noncontact Nonexpandable Catheter: A Feasibility Study", *Annals of Biomedical Engineering*, 26:994-1009, 1998.
Lorensen et al. "Marching Cubes: A High Resolution 3D Surface Construction Algorithm". Computer Graphics 21(4):163-169, Jul. 1987.
Mäkelä et al., "A Review of Cardiac Image Registration Methods", *IEEE Transactions on Medical Imaging*, 21(9):1011-1021, 2002.

Malladi, R. et al., "A Geometric Approach to Segmentation and Analysis of 3D Medical Images", Mathematical Methods in Biomedical Image Analysis, Proceedings of the Workshop on, Jun. 21-22, 1996, pp, 244-252, (1996).
Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).
Meininger et al., "Initial Experience with a Novel Focused Ultrasound Ablation System for Ring Ablation Outside the Pulmonary Vein", *Journal of Interventional Cardiac Electrophysiology*, 8:141-148, 2003.
Merrill, Daniel R. et al., "Electrical stimulation of excitable tissue: design of efficacious and safe protocols", Journal of Neuroscience Methods, vol. 141, pp. 171-198 (2005).
Miller, "Editor's Forum—Application of Registration for Ablation: A Marriage of Technologies", *Journal of Interventional Cardiac Electrophysiology*, 11:87-89, 2004.
Nademanee et al., "A New Approach for Catheter Ablation of Atrial Fibrillation: Mapping of the Electrophysiologic Substrate", *Journal of the American College of Cardiology*, 43(11):2044-2053, 2004.
Noseworthy et al., "The Impact of Respiration on Left Atrial and Pulmonary Venous Anatomy: Implications for Image-Guided Intervention", *Heart Rhythm*, 2:1173-1178, 2005.
Notification of Transmittal of the International Search Report and the Written Opinion of the International Searching Authority, or the Declaration, 15 pages, Sep. 12, 2008.
Notification of Transmittal of the International Search Report and the Written Opinion of the International Searching Authority, or the Declaration, PCT/US2009/036099, Dated Apr. 28, 2009, 21 pages.
Pappone et al., "Robotic Magnetic Navigation for Atrial Fibrillation Ablation", *Journal of the American College of Cardiology*, 47(7):1390-1400, 2006.
Paragios, "A Level Set Approach for Shape-Driven Segmentation and Tracking of the Left Ventricle", *IEEE Transactions on Medical Imaging*, 22(6):773-776, 2003.
Persson et al., "A Simple Mesh Generator in MATLAB", *SIAM Review*, 46(2):329-345, 2004.
Persson, "Mesh Generation for Implicit Geometries", *Massachusetts Institute of Technology—Thesis*, Feb. 5, 2006.
Pham, Dzung et al., "Current Methods in Medical Image Segmentation", Annu. Rev. Biomed. Eng., 02: pp. 315-337, (2000).
Rao et al., "Novel Noncontact Catheter System for Endocardial Electrical and Anatomical Imaging", *Annals of Biomedical Engineering*, 32(4):573-584, 2004.
Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", *Journal of the American College of Cardiology*, 44(11):2202-2213, 2004.
Reddy et al., "Use of a Diode Laser Balloon Ablation Catheter to Generate Circumferential Pulmonary Venous Lesions in an Open-Thoracotomy Caprine Model", *PACE*, 27:52-57, 2004.
Sanders et al., "Spectral Analysis Identifies Sites of High-Frequency Activity Maintaining Atrial Fibrillation in Humans", *Circulation*, 112:789-797, 2005.
Sethian. "Level Set Methods and Fast Marching Methods: Evolving Interfaces in Computational Geometry, Fluid Mechanics, Computer Vision, and Materials Science". *Department of Mathematics—University of California*, Berkeley. Cambridge University Press, 1999.
Simon et al., "Electroanatomic Mapping of the Right Atrium With a Right Atrial Basket Catheter and Three-Dimensional Intracardiac Echocardiography", *PACE*, 27:318-326, 2004.
Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.
Solomon et al., "Real-Time Cardiac Catheter Navigation on Three-Dimensional CT Images", *Journal of Interventional Cardiac Electrophysiology*, 8:27-36, 2003.
Sra et al., "Registration of Three-Dimensional Left Atrial Computed Tomographic Images With Projection Images Obtained Using Fluoroscopy", *Circulation*, 112:3763-3768, 2005.

Sra, Jasbir et al, "Registration of 3D Computed Tomographic Images With Interventional Systems: Implications for Catheter Ablation of Atrial Fibrillation", J Interv Card Electrophysiol, 16: pp. 141-148, (2006).

Stevenson, "Radiofrequency Catheter Ablation of Ventricular Tachycardia After Myocardial Infarction", *Circulation*, 98:308-314, 1998.

Taccardi et al., "A New Intracavitary Probe for Detecting the Site of the Origin of Ectopic Ventricular Beats During One Cardiac Cycle", *Circulation*, 75(1):272-281, 1987.

Thal et al., "Novel Applications in Catheter Ablation", *Journal of Interventional Cardiac Electrophysiology*, 13:17-21, 2005.

Thiagalingam et al., "Noncontact Mapping of the Left Ventricle: Insights from Validation With Transmural Contact Mapping", *PACE*, 27:570-578, 2004.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf et al., "LocaLisa: New Technique for Real-Time 3-Dimensional Localization of Regular Intracardiac Electrodes", *Circulation*, 99:1312-1317, 1999.

Yezzi, Anthony et al., "A Geometric Snake Model for Segmentation", IEEE Transactions on Medical Imaging, vol. 16, No. 2, (Apr. 1997).

CARDIAC MAPPING

CROSS REFERENCE TO RELATED APPLICATIONS

This application is a continuation and claims priority under 35 USC §120 to U.S. patent application Ser. No. 12/138,678, now U.S. Pat. No. 7,957,791, filed Jun. 13, 2008, which is a continuation of U.S. patent application Ser. No. 11/451,898, filed Jun. 13, 2006, now U.S. Pat. No. 7,515,954, the entire contents of which are hereby incorporated by reference.

TECHNICAL FIELD

This invention relates to the determination and representation of physiological information relating to a heart surface using a non-contact catheter.

BACKGROUND

Cardiac arrhythmias are a leading cause of stroke, heart disease and sudden death. The physiological mechanism of arrhythmia involves an abnormality in the electrical conduction of the heart. There are a number of treatment options for patients with arrhythmia which include medication, implantable devices, and minimally invasive procedures.

Minimally invasive procedures, such as catheter ablation, have evolved in recent years to become an established treatment for patients with a variety of supraventricular and ventricular arrhythmias. A typical minimally invasive procedure involves mapping of the heart tissue in order to identify the site of origin of the arrhythmia followed by a targeted ablation of the site. Other minimally invasive procedures involve the delivery of biological agents such as cells or genes as a form of therapy to the identified site of origin of the arrhythmia. The procedure takes place in an electrophysiology laboratory and takes several hours, most of which is spent mapping the electrical conduction in the heart.

Conventional 3D mapping techniques include contact mapping and non-contact mapping. In contact mapping techniques one or more catheters are advanced into the heart. Physiological signals resulting from the electrical activity of the heart are acquired with one or more electrodes located at the catheter distal tip after determining that the tip is in stable and steady contact with the endocardium surface of a particular heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm. Although the electrode(s) contacting the endocardium surface enable a relatively faithful acquisition of physiological signals with minimal signal degradation, contact-based mapping techniques tend to be time consuming since the catheter, and thus its electrodes, have to be moved to a relatively large number of locations in the heart cavity to acquire sufficient data to construct the electro-anatomical depiction of the heart. Additionally, moving the catheter to different locations so that the catheter's electrode(s) touch the endocardium is a cumbersome process that is technically challenging. Further complicating the contact-based mapping methodology is the occurrence of unstable arrhythmias condition. Particularly, ventricular tachyarrhythmias may compromise the heart's ability to circulate blood effectively. As a result, the patient cannot be maintained in fast tachyarrhythmia's for more than a few minutes, which significantly complicates the ability to map during the arrhythmia. In addition, some arrhythmia's are transient or non-periodic in nature. Contact-based sequential mapping, therefore, is less suitable for mapping these arrhythmia's since the sequential contact-based methodology is predicated on the assumption that recorded signals are periodic in nature.

On the other hand, in non-contact-based mapping systems a multiple electrodes catheter is percutaneously placed in the heart chamber of interest. Once in the chamber, the catheter is deployed to assume a 3D shape. Using the signals detected by the non-contact electrodes and information on chamber anatomy and relative electrode location, the system provides physiological information regarding the endocardium of the heart chamber. Although non-contact mapping techniques can simultaneously acquire signals using the multiple electrodes catheter and thus enable faster reconstruction of the electrical activity on the endocardial surface, because the catheter's multiple electrodes are not in contact with the endocardium surface some loss of accuracy of the reconstructed map, which is proportional to the distance from the endocardium, occurs due to the degradation of the signals acquired by the multiple electrodes. Moreover, the computation of the complex transformations required to transform the signals acquired by the catheter's electrodes to determine the corresponding reconstructed information at the endocardium surface is relatively time consuming. Also, the accuracy of the reconstructed information is constrained by the number of electrodes that can be attached to the catheter.

SUMMARY

In one aspect, a non-contact cardiac mapping method is disclosed that includes: (i) inserting a catheter into a heart cavity having an endocardium surface, the catheter including multiple, spatially distributed electrodes; (ii) measuring signals at the catheter electrodes in response to electrical activity in the heart cavity with the catheter spaced from the endocardium surface; and (iii) determining physiological information at multiple locations of the endocardium surface based on the measured signals and positions of the electrodes with respect to the endocardium surface.

Embodiments may further include one or more of the following features:

The method may further include moving the catheter to each of multiple, different positions in the heart cavity for which the catheter is spaced from the endocardium surface, and, for each of the different catheter positions, determining the positions of the catheter electrodes with respect to the endocardium surface and measuring signals at the catheter electrodes in response to electrical activity in the heart cavity. The determination of the physiological information at the multiple locations of the endocardium surface is based further on the positions of the catheter electrodes and the measured signals at the different catheter positions.

The number of catheter positions at which the signals are measured and used to determine the physiological information at the multiple locations of the endocardium surface may be more than three. In some embodiments the number of catheter positions at which the signals are measured is more than five, and in some other embodiments the number of catheter positions at which the signals are measured is more than ten.

Typically, the catheter is moved over a range larger than about one third of the diameter of the heart cavity to measure the signals used to determine the physiological information at the multiple locations of the endocardium surface.

The signals may be measured for at least one electrical heart cycle for each catheter position.

The determination of the physiological information at the multiple locations of the endocardium surface may include synchronizing the signals measured at the different catheter positions with one another according to an electrical heart beat cycle.

The measured signals may be synchronized based on physiological data including, for example, ECG and/or intercardiac electrograms.

The determination of the physiological information at the multiple locations of the endocardium surface may further include processing the synchronized signals as though they were obtained at one time from all of the positions sampled by the catheter electrodes for the different positions of the catheter in the heart cavity.

The determination of the physiological information at the multiple locations of the endocardium surface may further include applying a transformation function to the synchronized signals. The transformation function relates signals measured from at least some of the different positions of the catheter in the heart cavity to the physiological information at the multiple locations of the endocardium surface.

The determination of the physiological information at the multiple locations of the endocardium surface may further include determining the transformation function by calculating a forward transformation for relating the physiological information at the multiple locations of the endocardium surface to the signals measured for the different positions of the catheter in the heart cavity and inverting the forward transformation. Inverting the forward transformation may include reformulating an underdetermined matrix inversion by regularization. Inverting may include a least squares minimization.

The determination of the physiological information at the multiple locations of the endocardium surface may include determining multiple estimates of the physiological information for each of at least some of the locations on the endocardium based on the measured signals corresponding to at least some of the different catheter positions. The method may include processing the multiple estimates to improve an accuracy of the physiological information. The processing of the multiple estimates may also include averaging the estimates. Averaging may be a weighted averaging.

Determining the position of the catheter electrodes with respect to the endocardium surface may include using, for example, electric fields, magnetic fields, fluoroscopy, and/or ultrasound to determine a position of the catheter in a first coordinate system. Determining the position of the catheter with respect to the endocardium surface may further include registering a representation of the endocardium surface with the first coordinate system, the representation having been obtained prior to inserting the catheter into the heart cavity.

The signals may be measured during multiple electrical heart beat cycles, and the physiological information may be determined, at least in part, by combining information derived from the signals for different heart beat cycles.

The combining may include integrating information derived from the signals for common phases of the electrical heart beat cycles. The integrated information may include integrated electric potentials on the endocardium surface for common phases of the multiple electrical heart cycle.

The information derived from the signals for different heart beat cycles may include, for example, a maximum voltage amplitude for each of the different heart beat cycles at different ones of the endocardium surface locations. The combining may include averaging together the maximum voltage amplitudes for the different heart beat cycles. The averaging may be a weighted averaging.

The method may further include generating a representation of the endocardium surface of a patient's heart cavity prior to inserting the catheter into the heart cavity, and registering the representation of the endocardium surface with a first coordinate system used to determine the positions of the catheter electrodes relative to the endocardium surface after the catheter is inserted into the heart cavity.

The determination of the physiological information at the multiple locations of the endocardium surface may be based on the positions of the catheter electrodes, the measured signals at the different catheter positions and the registered representation of the endocardium surface.

Generating the representation of the endocardium surface may include segmenting a volumetric representation of the heart cavity. The volumetric representation may be obtained from, for example, a coherence tomography (CT) image, a magnetic resonance imaging (MRI) image and/or an ultrasound image. The volumetric representation may be segmented into a substantially closed surface representation of the endocardium surface.

Generating the representation of the endocardium surface may include partitioning the representation into a plurality of surface elements based on, for example, a numerical calculation technique applied to facilitate computing of the physiological information at the endocardium surface and/or characteristics of the endocardium surface. The representation partitioned into a plurality of elements may include, for example, a surface mesh comprising triangles, a volumetric mesh comprising tetrahedra and/or a regular Cartesian grid.

The method may further include contacting the catheter to the endocardium surface at multiple locations to establish multiple points of the endocardium surface in the first coordinate system. The method may also include determining the position of the catheter when it contacts the endocardium surface at the multiple locations using, for example, electric fields, magnetic fields, fluoroscopy, and/or ultrasound to determine the position of the catheter in the first coordinate system. Registering may include translating and orienting the surface representation in the first coordinate system to fit the established points of the endocardium surface in the first coordinate system.

The determining of the physiological information may include, prior to inserting the catheter into the heart cavity, processing information relating to characteristics of the endocardium surface.

Processing information relating to characteristics of the endocardium surface may include partially computing one or more transformation functions for converting the signals measured at the catheter electrodes to estimates of the physiological information at the endocardium surface.

In some embodiments, each transformation function may be associated with a different position within the heart cavity.

In some embodiments, each transformation function may be associated with a different position and orientation of the catheter within the heart cavity.

In some embodiments, each transformation function may be associated with the respective positions of the catheter electrodes within the heart cavity.

Determining of the physiological information may further include, prior to inserting the catheter into the heart cavity, processing information relating to the characteristics of the catheter.

The characteristics of the endocardium surface may be derived from a pre-acquired representation of the endocardium surface.

The processing prior to inserting the catheter into the heart cavity may be performed to expedite the determination of the physiological information at the multiple locations of the endocardium surface from the measured signals.

The transformation functions may be inverse transformation functions, where the partial computation of the one or more inverse transformation functions may include at least partially computing one or more forward transformation functions for determining the signals measured at the catheter electrodes from the physiological information at the multiple locations of the endocardium surface, each forward transformation function being associated with the position of one or more catheter electrodes within the heart cavity. Each forward transformation function may further be associated with an orientation of the catheter within the heart cavity. The catheter may be hollow.

At least partially computing the one or more forward transformations may include processing information relating to the shape of the endocardium surface.

At least partially computing the one or more forward transformations may include processing information relating to the distribution of the electrodes on the catheter.

At least partially computing the one or more forward transformations may include fully computing the one or more forward transformations based on the information relating to at least the shape of the endocardium surface.

Determining the physiological information from the measured signals may include inverting the forward transformation function associated with the position of the catheter used to measure the signals and applying the inverted forward transformation function to the measured signals. Inverting the forward transformation may include reformulating an under-determined matrix inversion by regularization. Inverting may further include performing a least squares minimization. The inversion may further include a Tikhonov regularization.

The one or more transformation functions can be expressed as one or more matrices.

The method may further include computing values indicative of a degree of spatial resolution of the determined physiological information for at least some of the locations of the endocardium surface.

The computed values may be derived, at least in part, from a transformation function relating the physiological information at the multiple locations of the endocardium surface to the signals measured by the catheter electrodes.

The method may further include displaying at least a portion of the endocardium surface to include at least some of the computed resolution values. The method may further include overlaying on a display device at least some of the physiological information determined at the multiple surface locations.

The method may further include displaying at least a portion of the endocardium surface to include a selected subset of the physiological information determined at the multiple surface locations, where the subset is selected based on at least some of the computed resolution values.

The determined physiological information may include electrical potential values at the multiple locations of endocardium surface at different phases of the heart beat cycle. The method further may include determining frequency dependent features of converting the electrical potential values into a frequency representation of electrical activity at multiple locations of the endocardium surface during the heart beat cycle.

The method may further include displaying at least a portion of the endocardium surface to include information about the frequency representation at corresponding locations of the endocardium surface.

The information about the frequency representation may include information indicative of a dominant frequency in the frequency representation.

The method may further include using the determined physiological information to guide treatment of the heart cavity.

The treatment may include ablation of one or more selected regions of the heart.

The treatment may include cell therapy, gene therapy, or application of other biological agents.

The method may further includes repeating the measurement of catheter electrode signals and the determination of the physiological information after the treatment, and displaying a difference map including information about how the determined physiological information changed in response to the treatment.

The determined physiological information may include isopotential lines or bands corresponding to sets of contiguous locations of the multiple locations of endocardium surface having electrical potential values that are equal or within a selected range. The method may further include displaying at least a portion of the endocardium surface to include at least some of the isopotential lines. Displaying may include presenting the isopotential lines for each of different phases of the heart beat cycle.

The determined physiological information may include electrical potential values at the multiple locations of endocardium surface at different phases of the heart beat cycle, and the method may further include displaying at least a portion of the endocardium surface to include information about the electric potential values. Displaying information about the electric potential values may include, for example, the maximum electrical potential during the heart beat cycle for different locations of the endocardium surface and/or the root mean square of the electrical potentials during the heart beat cycle for different locations of the endocardium surface.

The determined physiological information may include an activation time for each of different locations of the endocardium surface. The method may further include displaying at least a portion of the endocardium surface to include representations indicative of the activations times. The activation times within a common activation time range are displayed with a common color or visual indication.

The number of locations on the endocardium surface where physiological information is determined may be more than 10 times more than the number of electrodes on the catheter.

The catheter may be spaced from the endocardium surface by more than about 3 mm when measuring the signals.

The method may further include displaying at least a portion of the endocardium surface to include at least some of the physiological information determined at the multiple surface locations.

The signals measured may be electrical signals. The signals measured may be electric potential signals.

The physiological information may be electrical information. The physiological information may include electrical potentials at the multiple locations of the endocardium surface at each of one or more phases of the heart cycle, and any information derivable there from, such as: isopotential maps, maximum or RMS voltage maps, activation time maps, and frequency maps.

Determining the position of the catheter electrodes may include measuring information about, for example, a position and/or orientation of the catheter within the heart cavity.

Determining the position of the catheter electrodes may be based further on information about the distribution of the electrodes on the catheter. Measuring information about, for example, a position and/or orientation of the catheter within the heart cavity may include measuring the position of one or more catheter electrodes within the heart cavity.

Determining the position of the catheter electrodes may include directly measuring the position of each catheter electrode within the heart cavity.

In another aspect, a system is disclosed that includes a catheter configured to be inserted into a heart cavity having an endocardium surface, the catheter including multiple, spatially distributed electrodes, the multiple electrodes configured to measure signals in response to electrical activity in the heart cavity with the catheter spaced from the endocardium surface. The system also includes a processing unit configured to determine physiological information at multiple locations of the endocardium surface based on the measured signals and positions of the electrodes with respect to the endocardium surface.

In certain embodiments, the system may further include a sensor device configured to interact with the processing unit to determine the positions of the catheter electrodes with respect to the endocardium surface.

Embodiments of the system may include any feature corresponding to any of the features as set forth above for the method. For example, the processing unit can be configured (e.g., programmed) to carry out one of more of the processing/determining type method steps described above.

In a further aspect, disclosed is a computer program product residing on a machine-readable medium for storing computer instructions that, when executed, cause a processor-based machine to receive from multiple, spatially distributed electrodes of a catheter, after the catheter has been inserted into a heart cavity having an endocardium surface, signals measured by the electrodes in response to electrical activity in the heart cavity, with the catheter spaced from the endocardium surface. The computer instructions also cause the processor-based machine to determine physiological information at multiple locations of the endocardium surface based on the measured signals and positions of the electrodes with respect to the endocardium surface.

Like the system aspect, embodiments of the computer program product may include any feature corresponding to any of the features as set forth above for the method.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Overview

Disclosed herein is a system and method for non-contact mapping and presentation of physiological information in relation to an endocardium surface of a heart chamber. In certain embodiments, the non-contact mapping system uses a movable multi-electrode catheter that is displaced to multiple locations within the heart chamber, thereby improving the resolution and accuracy of data that can be acquired by a single catheter. Transformation functions are computed prior to the commencement of signal measurement and acquisition of raw data to expedite the reconstruction process to assemble the physiological information provided to a user.

Figure 1:
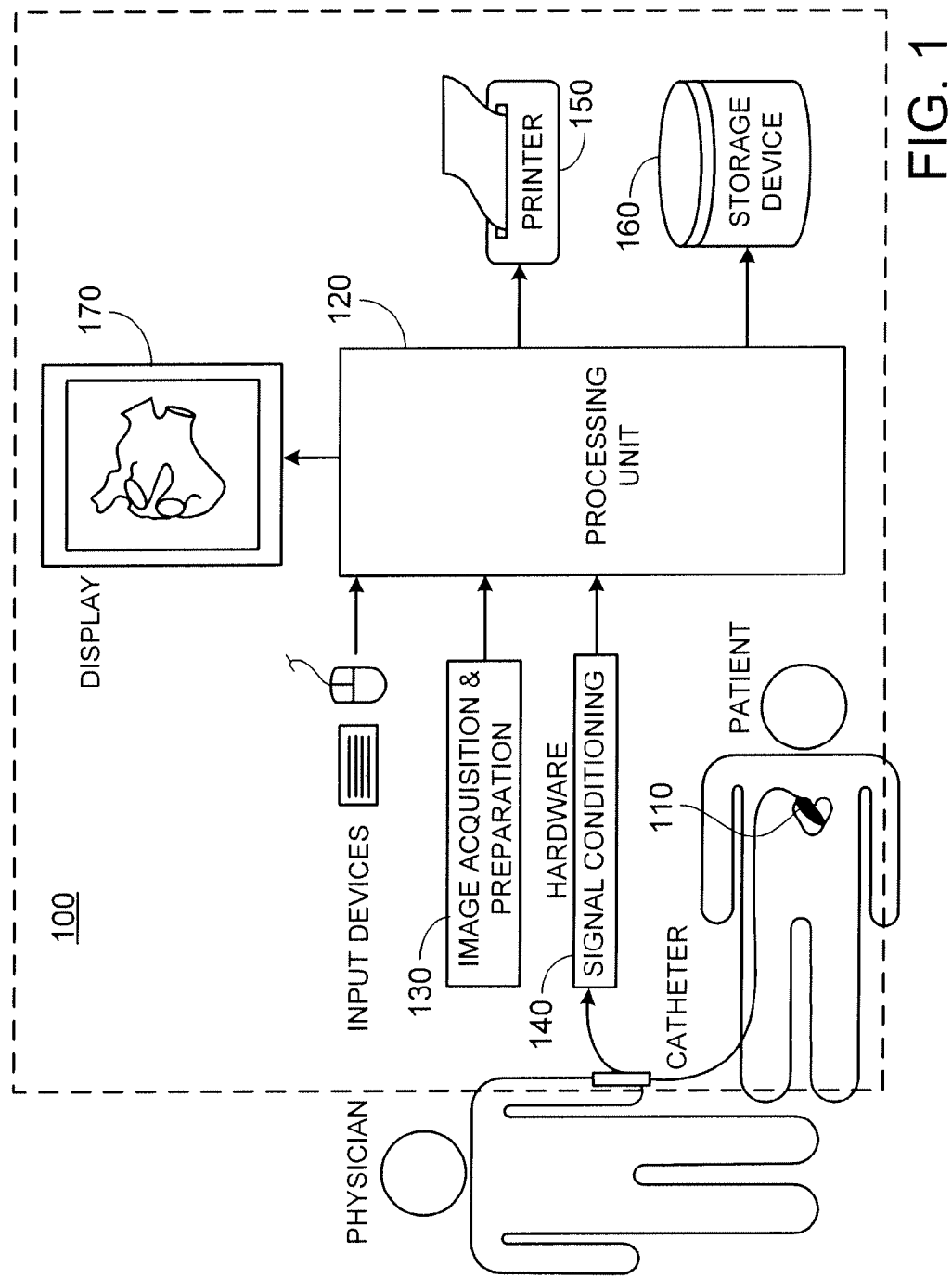
FIG. 1 is a schematic diagram of an exemplary non-contact mapping system.

FIG. 1 shows a schematic diagram of an exemplary embodiment of a non-contact system 100. The non-contact system 100 includes a moveable catheter 110 having multiple spatially distributed electrodes. During the signal acquisition stage of the non-contact mapping procedure the catheter 110 is displaced to multiple locations within the heart chamber into which catheter 110 is inserted.

In some embodiments the distal end of the catheter 110 is fitted with multiple electrodes spread somewhat uniformly over the catheter. For example, the electrodes may be mounted on the catheter 110 following a 3D olive shape. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, or shape memory material such as Nitinol.

At each of the locations to which the catheter 110 is moved, the catheter's multiple electrodes acquire signals resulting from the electrical activity in the heart cavity in a non-contact manner. Thus, at each of the locations to which the catheter 110 is moved, the catheter is spaced from the endocardium surface. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, as will be described in further details below, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements are synchronized with one another so that the measurement are performed at approximately the same phase of the heart cycle. The signal measurements over multiple beats can be synchronized based on features detected from physiological data such as surface ECG or intracardiac electrograms.

Non-contact mapping system 100 further includes the processing unit 120 which performs several of the operations pertaining to the non-contact mapping procedure, including the reconstruction procedure to determine the physiological information at the endocardium surface. As will be described in more details below, the reconstruction of physiological information (e.g., electrical potentials) at the endocardium surface includes the computations of transform functions corresponding to the solution of the partial differential equations that define the relationship between acquired signals measured by the catheter's multiple electrodes and the physiological behavior (e.g., the electrical potential behavior) of the endocardium surface. We generally refer to the "forward" transform or transformation as the mathematical operation that provides the signals measured by the catheter electrodes based on the electrical activity at different locations of the endocardium surface. Because there are typically many more endocardium surface locations than catheter electrodes this forward transformation is generally well-defined. We generally refer to the "inverse" transform as some type of mathematical inversion of this forward transformation to provide information about the electrical activity at the different locations of the endocardium surface based on the measured signals at the catheter electrodes. The reconstruction process also includes the computation of inverse transform functions based on a regularization scheme to determine the physiological information at the endocardium surface based on the acquired signals at the multiple electrodes. Thus, the computational effort involved in the reconstruction process is considerable.

Accordingly, to expedite the computational operations performed by the non-contact mapping system 100, the processing unit 120 can compute, generally prior to the insertion of the catheter into the heart chamber and/or before signal acquisition by the catheter's electrodes has commenced, transformation functions that can be used in real-time to facilitate the reconstruction process. More specifically, the transformation functions that are applied to the raw data can be represented in terms of individual transformation components. The individual transformation components include, for example, transformation components corresponding to chamber anatomy, and/or the geometry of the catheter. Thus, to expedite the reconstruction procedure for generating the endocardium surface's physiological information, the processing unit 120 computes transformation functions pertaining to the chamber's geometry and/or the catheter's geometry, and those components are combined during the reconstruction process with other transformation functions to form the overall inverse transform function.

Since the overall inverse transform that is applied to the raw data depends on the particular location of the catheter 110 (for example, position and/or orientation) in the heart chamber, in some embodiments the reconstruction process can be further expedited by pre-computing the forward transform for multiple catheter and/or electrode locations. Because forward transforms have to be computed individually for the possible catheter and/or electrode locations, the number of pre-computed forward transforms will be related to the number of possible locations that the catheter 110 may take in the heart chamber.

Once the catheter 110 is inserted and is displaced to a particular location in the heart chamber, the mapping procedure can be performed expeditiously by computing in real-time those transformation components that could not be computed ahead of the signal acquisition stage, and combining those components with the appropriate pre-processed transformation components to obtain the overall transformation function(s). That overall transformation function is applied to the acquired raw data to perform the inverse reconstruction operation.

In addition to computing the pre-processed partial transformation functions, the processing unit 120 also performs a catheter registration procedure. The location of the catheter 110 inserted into the heart chamber can be determined using a conventional sensing and tracking system (not shown) that provide the 3D spatial coordinates of the catheter and/or its multiple electrodes with respect to the catheter's coordinate system as established by the sensing and tracking system. However, to perform the mapping procedure and reconstruct physiological information on the endocardium surface, it is necessary to align the coordinate system of the catheter 110 with the endocardium surface's coordinate system. As will be described below in greater detail, the processing unit 120 (or some other processing module of system 100) determines a coordinate system transformation function that transforms the 3D spatial coordinates of the catheter's locations into coordinates expressed in terms of the endocardium surface's coordinate system, or vice-versa.

As will become apparent below, the processing unit 120 also performs post-processing operations on the reconstructed physiological information to extract and display useful features of the information to the operator of the system 100 and/or other persons (e.g., a physician).

As also shown in FIG. 1, the non-contact mapping system 100 includes the image acquisition and preparation module 130. The acquisition and preparation module 130 receives volumetric images (e.g., CT, MRI or ultrasound images taken by a scanner apparatus) of the torso, and processes them, using a procedure referred to as segmentation, to obtain a representation of the endocardium surface. Mapping of the data acquired by the multiple electrodes of catheter 110 is performed with reference to the representation of the endocardium surface. Once the boundary representation is constructed from the volumetric data, the boundary and or chamber volume representation is partitioned into elements whose characteristics are determined in accordance with, among other things, the types of numerical calculation techniques that are used to perform the mapping, as well as the overall geometry and characteristics of the endocardium surface as determined during the segmentation process from the acquired volumetric images.

As further shown in FIG. 1, the signals acquired by the multiple electrodes of catheter 110 are passed to the processing unit 120 via the signal conditioning module 140. The signal conditioning module 140 receives the signals communicated from the catheter 110 and performs signal enhancement operations on the signals before they are forwarded to the processing unit 120. Signal conditioning hardware is required to amplify, filter and continuously sample intracardiac potential measured by each electrode. The intracardiac signals typically have a maximum amplitude of 60 mV, with a mean of a few millivolts. In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal can be filtered to remove the frequency corresponding to the power supply (e.g., 60 Hz). Other types of signal processing operations such as spectral equalization, automatic gain control, etc. may also take place. The resultant processed signals are forwarded by the module 140 to the processing unit 120 for further processing.

In some embodiments, the signal conditioning module 140 is implemented by use of integrated components on a dedicated printed circuit board. In other embodiments, some of the signal conditioning tasks may be implemented on a CPU, FPGA or DSP after sampling. To accommodate safety regulations, the signal conditioning module is isolated from high voltage power supplies.

The processing unit 120, image acquisition and preparation module 130 shown in FIG. 1 is a processor-based device that includes a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading related content to the connected system. Such peripheral devices may also be used for downloading software containing computer instructions to enable general operation of the respective unit/module, and for downloading software implemented programs to perform operations in the manner that will be described in more detailed below with respect to the various systems and devices shown in FIG. 1. Alternatively, the various units/modules may be implemented on a single processor-based platform capable of performing the functions of these units/modules. Additionally or alternatively, one or more of the procedures performed by the processing unit 120 and/or image acquisition module 130 and/or signal conditioning module 140 may be implemented using processing hardware such as digital signal processors (DSP), field programmable gate arrays (FPGA), mixed-signal integrated circuits, etc. The signal conditioning module 140 is typically implemented using analog hardware augmented with signal processing capabilities provided by DSP, CPU and FPGA devices.

As further shown in FIG. 1, the non-contact mapping system 100 also includes peripheral devices such as printer 150 and/or display device 170, both of which are interconnected to the processing unit 120. Additionally, the non-contact mapping system 100 includes storage device 160 that is used to store data acquired by the various interconnected modules, including the volumetric images, raw data measured by electrodes and the resultant endocardium representation computed there from, the partially computed transformations used to expedite the mapping procedures, the reconstructed physiological information corresponding to the endocardium surface, etc.

Figure 2:
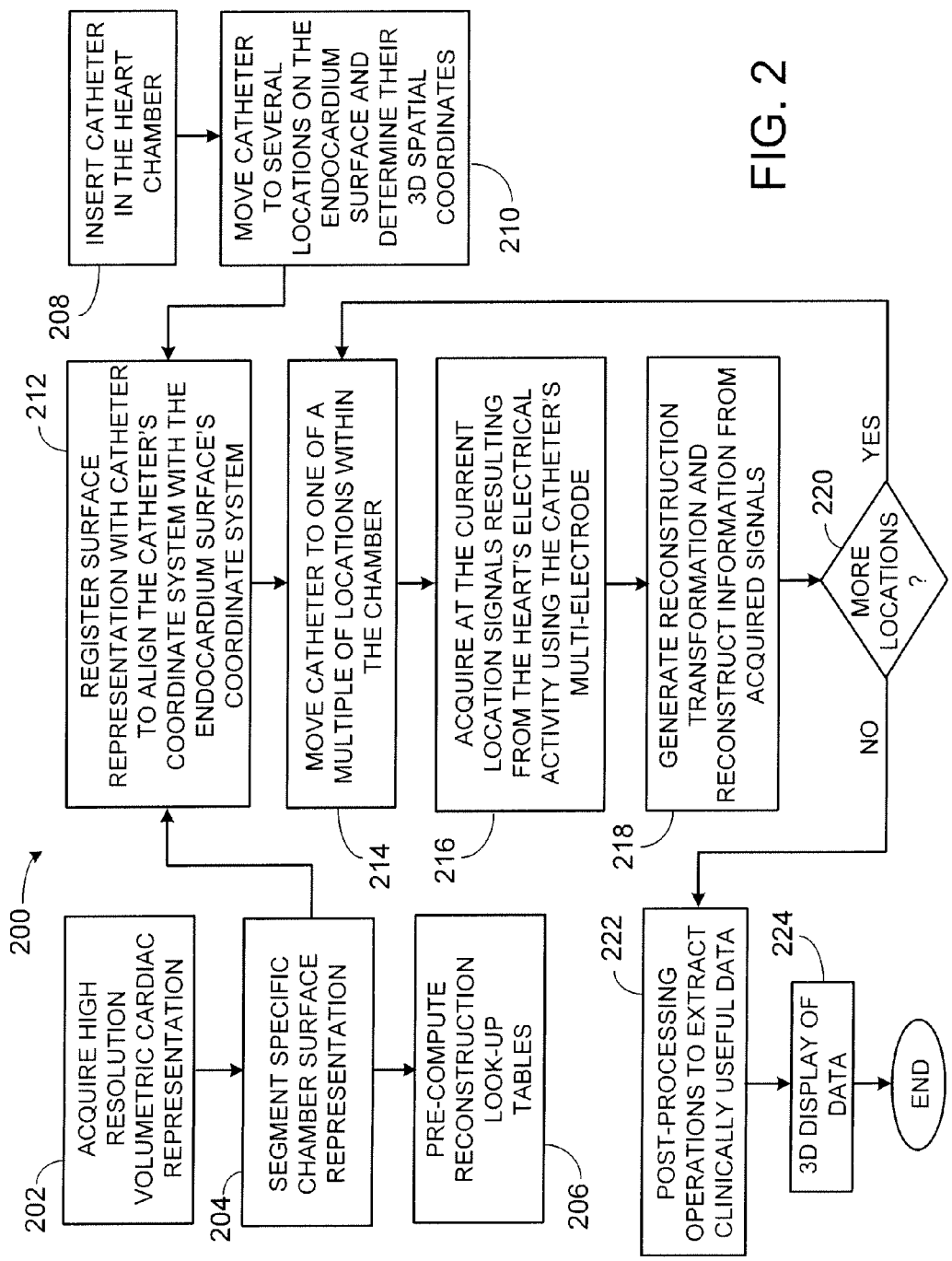
FIG. 2 is a flow diagram of an exemplary non-contact mapping procedure.

FIG. 2 is a flow diagram providing a top-level depiction of the various procedures performed by the system 100 in the course of performing the non-contact mapping procedure 200. As shown, the system 100 initially acquires at 202 volumetric cardiac representations of a patient's heart. Such volumetric representations may include high-resolution CT, MRI and/or ultrasonic slice images providing data regarding the geometry and characteristic of the patient's heart. The volumetric data may be acquired in advance of the commencement of other procedures comprising the non-contact mapping procedure. For example, the volumetric data may be obtained days or weeks prior to the catheter-insertion procedure. The volumetric data is initially received by the image acquisition and preparation module 130 shown in FIG. 1, but may subsequently be stored for future processing in storage module such as storage device 160.

Once volumetric data has been acquired, the image acquisition and preparation module 130 uses the acquired data to segment the volume, at 204, and provide a surface representation for a specific chamber into which the catheter will be inserted. The segmented volume is closed to allow numerical computations and partitioned to include surface elements whose geometry and/or other characteristics are based on the geometry of the surface representation, the type of numerical computation procedure used in the to generate forward transform functions, etc. In some embodiments, multiple endocardium surface representations may be generated, each of which corresponding to a different phase of the heart's cycle. For example, separate representations for the endocardium surface at multiple phases in the cardiac cycle such as systole and end diastole may be generated. Subsequent reconstruction of physiological information may then be performed with respect to the appropriate endocardium surface representation, depending at what phase of the heart cycle raw data was acquired.

With the geometries of catheter and the endocardium surface representation having been determined or otherwise known, the non-contact mapping procedure pre-computes at 206 transformation functions that thereafter can be quickly retrieved during the reconstruction of physiological information, thereby expediting the computation of the reconstruction transformations in real-time. The pre-processed transformation functions are represented and stored in the form of look-up tables, in the form of matrices, functional representations, or the like. Individual transformation functions correspond to one or more of the multiple locations within the heart chamber to which electrodes and/or the moveable catheter 110 may be moved during the non-contact mapping procedure. Other pre-computed transformations may correspond to the various heart shapes with respect to which the physiological information is determined. The pre-computed transformation functions may either be stored on a local storage module forming part of the processing unit 120, or may be alternatively stored on storage device 160.

The catheter 110 is inserted into the heart chamber to be studied at 208. The catheter 110 is typically inserted into the heart chamber via a suitable blood vessel leading to the heart chamber. In some embodiments, the electrodes of the catheter 110 are bundled into a compact configuration that enables the catheter 110 to be delivered to the heart chamber with minimal obstruction. Once inside the heart chamber, the electrodes of the catheter are deployed into a specified electrode arrangement relative to the catheter 110. During the mapping procedure 200, the moveable catheter 110 is displaced to multiple locations within the heart chamber, whereupon the catheter's electrodes acquire and record signals (e.g., electrical signals) resulting from the electrical activity of the heart.

As explained above, to reconstruct the physiological information of the endocardium surface, the system 100 applies reconstruction transformations on the signals acquired by the multiple electrodes of the catheter 110. Because the transformations applied to the acquired signals depends, among other things, on the location of the catheter relative to the endocardium surface, the mapping procedure first establishes the location of the catheter 110 with respect to the endocardium surface's coordinate system.

Accordingly, the non-contact mapping system 100 determines at 208 the 3D location of the catheter in a 3D coordinate system that corresponds to a sensing and tracking system used to locate the physical location of the catheter 110. In some embodiments, the location of the electrodes relative to the catheter 110 is fixed and known, and thus the only information that needs to be determined is the location and orientation of the catheter 110 in the 3D space established by the sensing and tracking system. Specifically, a sensor that is affixed to the catheter 110 may be used to determine the location and orientation of the catheter. In other embodiments the location and orientation of the various electrodes relative to the catheter may vary, and accordingly in such embodiments sensors attached proximate to the various electrodes may be used to facilitate the determination of the location of the catheter and/or its electrodes or by using a scheme that localizes electrode location using electrical impedance.

The sensing and tracking system employed to determine the 3D location of the catheter could be based, for example, on electromagnetic radiation tracking. In this method, electromagnetic fields are generated outside the patient body. A collection of miniaturized coils oriented to detect orthogonal magnetic fields forming a sensor are placed inside the catheter to detect the generated magnetic fields. A processing unit determines the location and orientation of the sensor based on amplitude and phase information in the signal detected by the multiple coils. Alternatively and/or additionally, the sensing and tracking system may be based on ultrasound, impedance or fluoroscopy tracking. In impedance and fluoroscopy tracking it is possible to locate the electrode location without necessitating dedicated sensors. In the case of impedance, electrical potential generated by electric field generators are detected by the existing electrodes. In case of fluoroscopy, electrode location may be detected by an image processing scheme that identifies and tracks the electrodes and/or opaque markers located on the catheter.

As will be described in greater details below, to perform the registration procedure, the 3D coordinates of the catheter 110 at various locations on the endocardium surface are determined. Thus, as shown at 210, an operator moves the catheter 110 inside the heart chamber until it determines that the catheter, or one or more of its electrodes, touches the endocardium surface. The 3D spatial coordinates of the catheter (and/or its electrodes) at that point on the endocardium surface is determined. The operator then moves the catheter 110 to additional points on the endocardium surface, and the 3D coordinates of the catheter 110 relative to the sensing and tracking system employed, at those additional points on the endocardium surface are determined.

It will be appreciated that while the 3D spatial coordinates of the catheter at various points on the endocardium surface relative to the sensing and tracking system's coordinate system are known, the identity of those points on the endocardium surface is not known. In other words, neither the identity nor the actual coordinates (with respect to the endocardium surface's coordinate systems) of the points at which the catheter touches the endocardium surface are known.

Accordingly, to determine the identity of the endocardium surface points corresponding to the catheter's 3D spatial locations, and thus determine the relationship between the endocardium surface's coordinate system and the catheter's 3D coordinate system, the two coordinate system have to be aligned. To align the two coordinate systems, a coordinate system transformation is computed at 212 that best matches the 3D locations of the catheter 110 at the endocardium surface, as determined at 210, to points on the endocardium surface that was determined at 204. Put another way, since the general geometry of the endocardium surface is known (from the computation at 204), and since the 3D coordinates at several points where the catheter 110 touches the endocardium surface are likewise known, the alignment procedure determines the optimal transformation that would cause the endocardium points expressed in the catheter's 3D coordinate system to be congruent with the endocardium surface representation that was determined from the volumetric data. Optimization techniques, such as least-square error computation procedures and/or other mathematical regression and curve-fitting techniques, are used to align the catheter's 3D coordinate system and the endocardium surface representation. In some embodiments the determination of the transformation function that aligns the two coordinate systems can be based on as few as three (3) points on the endocardium surface with respect to which the 3D spatial coordinates have been determined. More points may be used to compute the transformation function, depending on the desired accuracy and the acceptable computation effort that may be undertaken.

In some embodiments, the catheter registration procedure to align the endocardium surface's coordinate system with the coordinate system used to determine the 3D location of the catheter 110 yields a six (6) parameter transformation that includes three (3) displacement parameters ($x_0$, $y_0$, $z_0$) and three rotation parameters ($\theta_0$, $\phi_0$, $\psi_0$). These transformation parameters are subsequently applied to 3D spatial coordinates obtained by the sensing and tracking system used to determine the catheter's spatial coordinates to obtain the catheter's locations in terms of the endocardium surface's coordinate system.

Advantageously, generating a representation of the endocardium surface based on the pre-acquired volumetric data separately from determining the location of the catheter relative to the endocardium surface provides an accurate representation of the endocardium surface not attainable by sequential contact mapping.

Once the registration procedure is performed, the catheter 110 is moved, at 214, to a first location within the heart chamber in which the first set of measurement by the catheter's multiple electrodes is performed. Control of the catheter's movement and location within the heart chamber is performed manually by the operator manipulating the catheter 110. Alternatively, the movement of the catheter 110 within the heart chamber may be automated by use of techniques such as magnetic (see, e.g., Stereotaxis, Inc. of St. Louis, Mo.) or robotic (see, e.g., Hansen Robotics, Inc.) navigation. Catheter manipulation may be used to cause the catheter to follow a pre-determined displacement route to collect data at locations that may be considered to be of higher interest than others. For example, in some embodiments the catheter 110 may be moved at specified displacement intervals in an area of the heart chamber that is known have abnormal cardiac activity.

The 3D location of the catheter 110 is then determined using one of the techniques discussed previously 110 and/or to its multiple electrodes, thereby providing the catheter's spatial location in the catheter's coordinate system. The coordinates of the catheter 110 and/or its multiple electrodes relative to the endocardium surface (i.e., in the endocardium's coordinate system) are then computed using the coordinate system transformation function determined at 212.

At its current location, the multiple electrodes of the catheter 110 acquire at 216 signals resulting from the heart's electrical activities. In some embodiments the signals are electrical signals (e.g., potential, current, magnetic, etc.).

The non-contact mapping system 100 generates at 218 reconstruction transformation functions to be applied on the acquired signals to reconstruct the physiological information at the endocardium surface. The generated reconstruction transformation functions are based, among other things, on the pre-computed reconstruction transformation functions that were determined at 206, and the catheter's location relative to the endocardium surface. Thus, in some embodiments, for every location of the catheter 110 at which raw data is acquired, a corresponding set of reconstructed physiological information is computed.

As further shown in FIG. 2, after the raw data corresponding to the heart's electrical activity has been acquired, recorded and processed using reconstruction transformation function(s) to obtain reconstructed physiological information at the endocardium surface, a determination is made, at 220, whether there are additional locations within the heart chamber to which the catheter 110 is to be moved. If there are additional locations in the heart chamber to which the catheter 110 needs to be moved the catheter is moved, using manual or automatic control, to the next location in the heart chamber, whereupon the operation described in relation to the blocks 214-218 in FIG. 2 are performed for that next location.

Alternatively, in some embodiments, a composite resultant set of physiological information can be generated by selecting from multiple sets of reconstructed physiological information portions of the reconstructed information. As will become apparent below, selecting which portions of reconstructed information to use can be based on resolution maps that are indicative of the quality of the reconstructed information for a particular portion or set of the reconstructed physiological information. Other criteria and technique for selecting suitable portions of data to reconstruct a composite set of physiological information may be used.

Alternatively, in, some embodiments, one (or more) composite reconstruction transformation function is computed that is applied collectively to the raw data acquired at multiple locations to generate a resultant composite set of reconstructed physiological information based on a substantial part of the data acquired. Such a transformation function represents a "mega transformation function" that corresponds to the "mega catheter" referred to above, whose effective number of electrodes and electrode span is related to the number of locations to which the catheter was moved within the heart chamber. Under those circumstances the generation of the composite reconstruction transformation function is deferred until data is collected from the catheter's multiple locations.

Alternatively, in some embodiments, the "mega transformation function" and "mega catheter" may be updated on an ongoing basis to take into account a given relevant measurement window. This window may be a fixed number of measurements such that the arrival of new measurements displaces measurements that were obtained before the time window. This yields a constantly updating moving average.

In some embodiments, signals are measured throughout a heart beat cycle (for example, a measurement can be made at each catheter electrode at each of multiple, different phases of a single beat heart cycle).

Yet in further embodiments the reconstructed set of physiological information is computed based on measurements taken over one or more heart beats. In the latter situation, the catheter is moved to a particular location, and acquires multiple sets of raw data over several heart beats. The acquired data is averaged, and the reconstruction process is applied to the averaged values. As will become apparent below, if the data is acquired over B heart beats (i.e., B measurements), an improvement in the signal-to-noise ratio proportional to $\sqrt{B}$ is obtained. The timing of the measurement operation is generally synchronized to ensure that measured data is acquired at approximately the same phase of the heart cycle.

If it is determined at 220 that there are no additional locations within the heart chamber at which data needs to be collected, then the non-contact mapping system performs at 222 post-processing operations on the reconstructed physiological information to extract clinically useful data. As noted, in some embodiments the non-contact mapping system 100 produces a composite reconstructed set of physiological information. Post processing operation are performed, under those circumstances, on the composite set of reconstructed physiological information. In some circumstances where the non-contact mapping system 100 produces multiple reconstructed sets of physiological information for the raw data collected at each location in the heart chamber to which the catheter 110 was moved, the post processing operations are performed individually on one or more sets of reconstructed physiological information.

In some embodiments, the post processing may involve nothing further then selecting a format for outputting (e.g., displaying) the reconstructed potentials to a user. In other embodiments, the post-processing may involve significant further mathematical manipulation of the reconstructed potentials to provide additional types of physiological information.

The reconstructed physiological information and/or sets of post-processed data are then displayed at 224. The information, be it the reconstructed physiological information or any data resulting from the post-processing performed at 222, is displayed on a 3D graphical rendering of the representation of the endocardium surface generated at 204.

Some of the post-processing operations performed on the reconstructed set(s) of physiological information include the generation of a resolution map. Such a resolution map indicates the spatial resolution of physiological information at points on the endocardium surface, thereby providing a measure of the reliability and accuracy of the information at various points on the endocardium surface. The resolution map may also be used to form a composite set of reconstructed physiological information by associating with individual sets of acquired raw data and/or individual sets of reconstructed physiological information corresponding resolution maps. A resultant composite set is then formed by selecting portions of acquired raw data (or reconstructed information) whose reliability or accuracy, as indicated by the resolution map corresponding to the set from which the data is selected, is sufficiently high. Resolution maps may be used with any form of post-processing operation including all modes listed below. Strictly speaking, information about the resolution maps can be determined prior to obtaining the reconstructed potential data; however, herein we generally refer to the generation and display of the resolution map as "post-processing" because such information is typically presented to the user after at least some of the potentials are reconstructed.

Another type of post-processing operation that may be performed includes the generation of isopotential maps. Particularly, where the reconstructed physiological information pertains to electrical potentials, the reconstructed potentials may be color coded and superimposed on the 3D endocardial representation. Isopotential maps are the reconstructed potentials computed for every sampled set of data over a single or multiple heart beats.

Yet another type of post-processing operation includes the generation of timing maps (such as activation time maps). The timing maps provide information on the time-dependent behavior of the heart's electrical activity. Particularly, the activation map indicates at what point in time particular points on the endocardium surface experience a change in their electrical activity. For example, the activation map could identify the point in time at which particular cells on the endocardium surface experienced depolarization. Another type of timing map may be an iso-duration map where the amount of time certain tissue has been active for is detected. Timing maps may be computed from the reconstructed potentials over a single or multiple heart beats. Timing maps may be determined and displayed for one or more points on the endocardium surface representation.

Another type of post processing operation that may be performed at 222 is the generation of voltage maps. Voltage maps can be used to display characteristics of voltage amplitude in a given area. The voltage maps may be computed from the reconstructed potentials over a single or multiple heart beats. Useful voltage map information that may be determined and displayed for one or more points on the endocardium surface representation includes the maximum amplitude, or root mean square potential values.

Another type of post-processing operation is the generation of a difference map. The difference map provides information regarding the effectiveness of the clinical procedure (e.g., ablation) performed on the patient to ameliorate the symptoms of arrhythmias. The difference map compares the electrical behavior of the heart, as reflected from two or more voltage maps generated before and after the performance of the particular clinical procedure.

A further type of post processing operation is the generation of frequency maps. Frequency mapping, and more generally spectral analysis, are used to identify on the endocardium surface localized sites of high-frequency activity during fibrillation. Frequency maps are computed by acquiring multiple sets of reconstructed information over a particular time interval which includes a single or multiple heart beats. The acquired raw data is then used to obtain the frequency representation of that data. Specific information (e.g., dominant frequency components) from the frequency representation is subsequently identified, and that identified information may be displayed.

Other types of post-processing information may likewise be performed at 222.

The various procedures described above will now be described in greater detail.

Boundary Construction Procedure

As noted above, physiological information is reconstructed for an endocardium surface representation that is generated from pre-acquired volumetric data obtained using such techniques as coherence tomography (CT) imaging, magnetic resonance imaging (MRI) techniques, and/or ultrasound-based imaging technique. The volumetric data can be obtained in advance of the performance of the signal acquisition and/or the reconstruction procedure, or it can be obtained substantially concomitantly with the performance of either of these procedures. As described in further detail below, in preferred embodiments, for example, volumetric data, represented as image slices, can be acquired before the catheter 110 is inserted into the heart chamber that is to be mapped.

Acquisition of the volumetric data is performed using conventional scanning apparatus, such as CT, ultrasound, or MRI scanners, that provide acquired volumetric images to the image acquisition and preparation module 130. In preferred embodiments, the acquired image is usually stored and transferred in industry standard, e.g., DICOM format.

In order to facilitate the boundary construction procedure, the volumetric images may be acquired under a customized protocol. To facilitate the identification and construction of the endocardium surface (sometimes referred to as the blood-to-endocardium-boundary) from the acquired volumetric images, contrast agents may be injected into the body during image acquisition. The injection is timed such that the contrast agent is present in the endocardium during the acquisition time.

Since the heart contracts during imaging, additional physiological information is recorded and incorporated with image data during acquisition time. Parameters such as EKG and respiration phase enable matching the volumetric images to the specific phase of the heart and respiratory cycle.

To generate a representation of the endocardium surface from high resolution volumetric data, one first retrieves the volumetric data either from the image acquisition and preparation module 130 or from storage device 160. While the pre-acquired volumetric images are of high quality, in their original form they do not provide explicit information about the endocardium boundary. Accordingly, a boundary representation of the endocardium surface is generated based on the volumetric data using a procedure known as segmentation.

The segmentation algorithm detects the blood to endocardium boundary using the difference in corresponding contrast enhanced by the injected contrast agent. The segmentation may be performed utilizing one of a number of algorithms. One such algorithm is seeded region growing. The basic approach of the algorithm is to start from a seed region (typically one or more volume pixels, denoted voxels) that are considered to be inside the object to be segmented. The voxels neighboring this region are evaluated to determine if they should also be considered part of the object. If so, they are added to the region and the process continues as long as new pixels are added to the region.

The evaluation criteria for inclusion as part of the region may be based, for example, on algorithm based on statistical properties of the region. First, the algorithm computes the mean and standard deviation of intensity values for all the voxels currently included in the region. A user-provided factor is used to multiply the standard deviation and define a range around the mean (for example 3×). Neighbor voxels whose intensity values fall inside the range are accepted and included in the region. When no more neighbor voxels are found that satisfy the criterion, the algorithm is considered to have finished its first iteration. At that point, the mean and standard deviation of the intensity levels are recomputed using all the voxels currently included in the region. This mean and standard deviation defines a new intensity range that is used to visit current region neighbors and evaluate whether their intensity falls inside the range. This iterative process is repeated until no more voxels are added or the maximum number of iterations is reached.

A number of segmentation techniques may be used to perform segmentation. A number of commercially available and open source segmentation tools may be used to perform boundary detection. For example, these include Cardiac ++ by GE Healthcare systems, Amira by Mercury Computer Systems, and the open source National Library of Medicine Insight Segmentation and Registration Toolkit (ITK).

Figure 3:
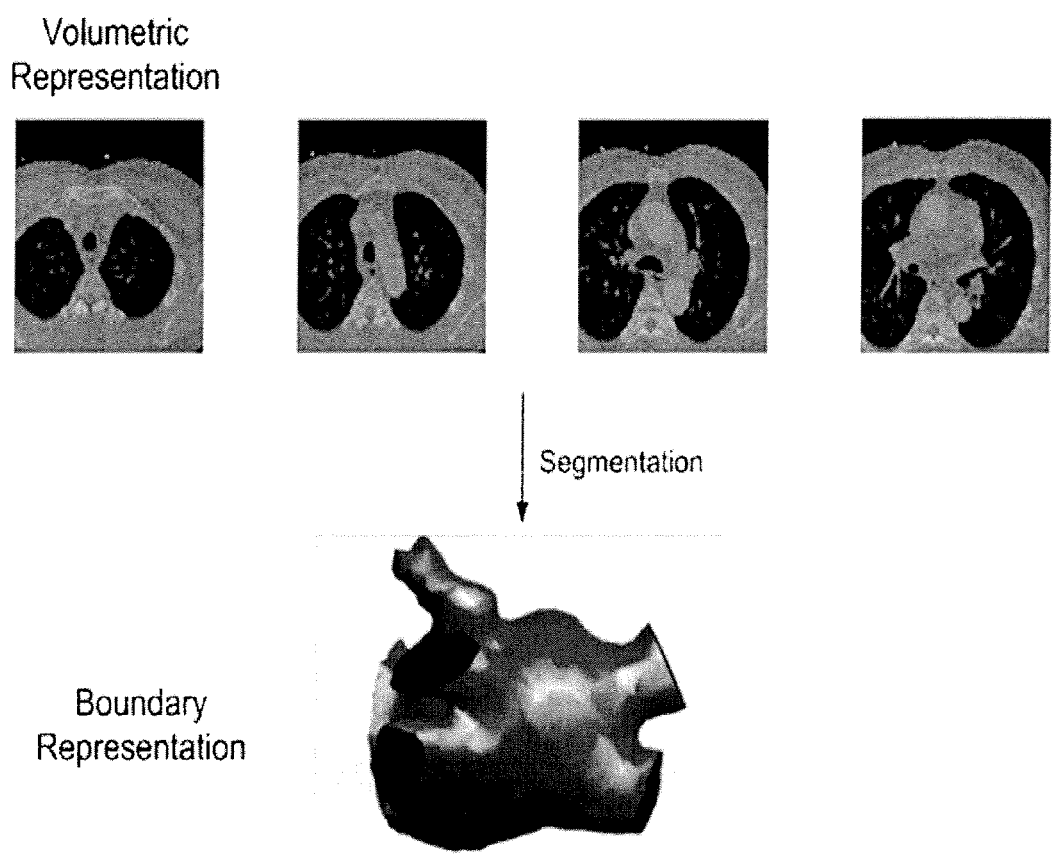
FIG. 3 is an exemplary illustration of a representation of the endocardium surface.

FIG. 3 provides an exemplary illustration of a resultant boundary representation of the endocardium surface produced from the acquired high resolution volumetric data after the performance of segmentation. As shown in FIG. 3, representative volumetric data comprising four image slices of the heart cavity are processed using a segmentation technique to generate the 3D boundary representation of the endocardium surface.

Once the endocardium representation has been obtained from the volumetric data, the anatomical geometry of the endocardium representation is partitioned into a discrete number of surface elements to facilitate the performance of the numerical computations that have to be undertaken during the reconstruction process. The number of surface elements, as well as their geometry, controls the maximum attainable resolution of the eventual reconstructed physiological information.

The partitioning of the segmented endocardium surface representation depends, among other things, on the numerical computation method used to solve the relevant partial differential equations (PDE's) that define the relationship between the physiological information at the endocardium surface and the measured signals. For example, finite differences (FD) and finite volume numerical methods, as well as the immersed boundary adaptation of the finite difference numerical method, use regular Cartesian grids. The finite element Method (FEM) numerical method uses volumetric meshes, often built from tetrahedra. On the other hand, the boundary element method (BEM), which is based on integral equations, uses a surface mesh generally comprising triangle-shaped surface elements, although higher order elements, such as splines, may similarly be used. It is to be noted that an advantage of the BEM method is that implementation of the BEM method to perform the computation needed to solve the PDE's in the course of the reconstruction process results in the generation of a non-varying mesh that does not change for different catheter positions.

In some embodiments the endocardium surface representation obtained is partitioned by using the Strang-Persson approach. Briefly, the approach is based on a mechanical analogy of a stable equilibrium truss consisting of weights and springs. The method assumes that the boundary is supplied as a signed distance function. A signed distance function refers to a three dimensional grid of data that contains the values of the function phi that represents the signed distance (<0 if inside, >0 if outside) from a given point to the boundary. The signed distance function may be readily obtained following the segmentation process described above.

The Strang-Persson approach places a number of nodes inside the domain and imagines that there is a compressed string along each edge that is created by Delaunay triangulation. The method then allows each spring to relax to its equilibrium length insomuch as it is constrained by other strings and as long as no node goes outside of the domain. If the nodes travel a significant distance, then Delaunay triangulation is repeated. This procedure is considered to be robust and produces high quality meshes.

It will be appreciated that other partitioning techniques may be used to partition the endocardium surface representation.

One problem that remains after the segmentation and partitioning procedures described above has been performed is the existence of geometrical discontinuities in the generated meshed representation of the endocardium surface. Elliptic equations, which correspond to a broad category of PDE's that includes the Laplace and Poisson equations, are solved with respect to closed domains for which a boundary condition is specified with respect to every point on the boundary. If boundary conditions are not specified along some part of the boundary, the solution for the PDE's is not uniquely defined. As a result, in addition to the correct solution there will be incorrect solutions for the particular PDE's to be solved that will satisfy the specified conditions. This property of elliptic equations (i.e., that undefined boundary conditions may yield incorrect solutions) is inherent to any numerical method. Thus, in some embodiments, the geometry of the endocardium surface is closed. Thus, for example, when applying the BEM numerical method using triangle-shaped surface elements, the endocardium surface, as well as the surface of the catheter, have to be represented by meshes having no gaps or overlaps.

Accordingly, having generated the partitioned endocardium surface representation, all openings on the representation (e.g., arteries or veins extending from the endocardium surface) are typically closed. The opening in the geometry of the endocardium representation can be closed with surface sections providing the shortest distances between any given point along the perimeters of the openings on the endocardium surface representation. Alternatively, geometries satisfying different criteria for the sections used to patch the openings in the endocardium surface representation may be used. Additionally, the sections that have been added to the representation where opening previously existed are partitioned to surface elements having the same geometry as the surface elements used in endocardium surface representation. Thus, in embodiments where the Strnag-Persson approach had been used to partition the endocardium surface into a mesh with triangle-shaped surface elements, the surface sections now covering the openings also include triangle-shaped surface elements. Subsequently, the solutions of the PDE's that will result in the reconstructed physiological information at the endocardium surface will include information pertaining to the added sections covering the opening. However, when presenting the physiological information to a user, or when displaying a graphical rendering of the endocardium surface representation, the added sections covering the actual openings in the surface should be excluded.

Accordingly, upon performing the boundary construction procedure, a resultant meshed representation of the endocardium surface is produced. That meshed representation of the endocardium surface satisfies the following requirements:
1. Closed Surface—as mentioned above, all surfaces must be closed. Prior segmentation techniques produce meshes that fully represent the veins and arteries. For the purposes of implementing numerical techniques, the veins and arteries must be effectively closed off with high quality meshes. The closed surfaces covering the veins and arteries in the derived representation of the endocardium surface may be subsequently removed prior to displaying the reconstructed physiological information or prior to otherwise making any use with the reconstructed physiological representation
2. Element Number—the number of surface elements should be high enough to resolve the geometry but, on the other hand, to the extent that the resultant geometry is adequately resolved, be as coarse as possible to facilitate speedy numerical computations. Endocardium surface representation that include too many surface elements (e.g., triangles) to accommodate unimportant local features of the geometry should be avoided.

3. Element Quality—The surface elements should be of high quality. The quality of a triangle-shaped surface element, for example, is a measure of how close it is to being equilateral. A simple measure of the triangle quality is the "radius ratio". The radius ratio is defined as the ratio of the radius of the circumscribed circle and that of the inscribed circle. The smaller the value, the higher the quality of the triangle. An equilateral triangle yields a radius ratio of 2, which is the lowest attainable value. The quality of the entire mesh can be measured as the average quality of the individual surface elements. However, some numerical computation techniques, such as FEM, are known to be sensitive to the quality of the worst triangle. It will be appreciated that the other quality metrics, pertaining to different types of surface element geometry may be used.

Figure 4:
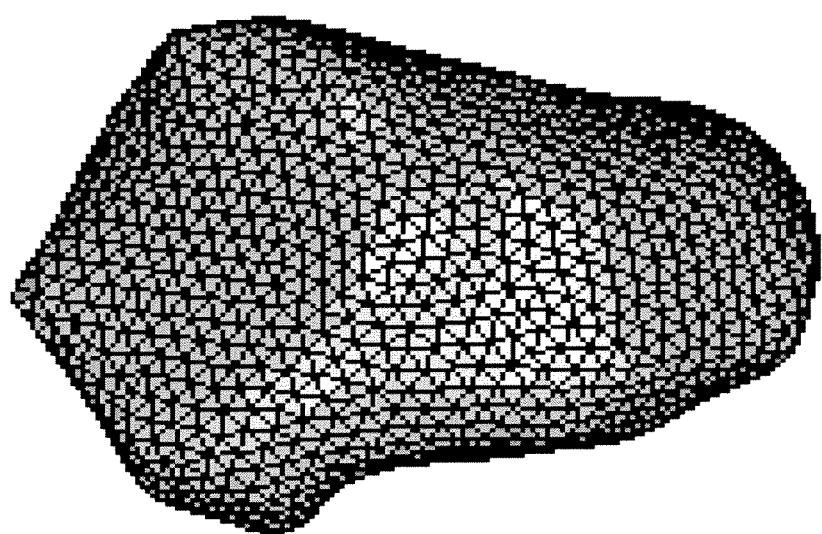
FIG. 4 is an exemplary illustration of a meshed boundary representation of an endocardium surface of a left atrium.

FIG. 4 is an exemplary illustration of a resultant meshed boundary representation of an endocardium surface of a left atrium generated by performing the procedure described herein. As shown, the boundary representation of the left atrium includes a mesh of triangular surface elements.

As described herein, physiological data obtained during the acquisition of the volumetric data may be used to enable the matching of volumetric images to the specific phase of the heart's mechanical cycle. In addition, in some embodiments, reconstructed physiological information obtained by performing of the non-contact mapping procedure could be presented on endocardium surface representation that most closely matches the mechanical phase of the heart during which the raw data resulting from the heart's electrical activity was acquired. Thus, in those embodiments, separate representations of the endocardium surface can be generated for different phases of the heart's cycle using the boundary construction procedure. Raw data acquired during a particular phase would then be reconstructed with respect to the representation of the endocardium surface corresponding to that phase. As described herein, the reconstruction transformations and catheter registration procedure are performed with respect to that particular representation of the endocardium surface. Similarly, the reconstructed physiological information is subsequently displayed using the corresponding endocardium surface representation. In circumstances where the raw data is acquired at a phase that does not have a corresponding endocardium surface representation, the reconstruction operations will be performed using the closest matching endocardium surface representation.

Pre-Computed Transformation Functions

As explained above, some of the computations involved in computing the reconstruction transformation are complex and time consuming. It is therefore preferable not to perform all of them in the clinical setting where physician interaction is required.

Because endocardial boundary and catheter geometries are known in advance, it is possible to perform computations corresponding to the reconstruction procedure, for example, computations pertaining to the forward transform, before the reconstruction procedure is performed, and store the pre-computed transform functions in memory for later use. When performing the reconstruction procedure, the pre-computed transformation functions can be retrieved from storage and used to compute the overall forward transform, thereby expediting the computation of the overall forward transform in real-time.

The reconstructed sets of physiological information are the solutions to elliptic partial differential equations (PDE's) that arise from Laplace's equation. To solve an elliptic PDE, a multi-variable function is defined on the closed domain that satisfies two properties: the bulk equation inside the domain (in the present case, e.g., blood) and the boundary conditions (in the present case, e.g., the endocardium and catheter).

Conventional numerical techniques used to compute solutions for PDE's convert PDE problems into a set of algebraic equations. Some components of these algebraic equations depend only on the geometry and the nature of the bulk equation, and others components depend on the boundary conditions. While the boundary conditions are not necessarily known during the pre-computation phase, much is known about the geometry. For example, the shape of the heart's cavity and the shape of the catheter are both known in advance of the signal measurement and reconstruction processes. Therefore, components of the transformation functions (or in some circumstances, the complete transform functions) are computed prior to the acquisition of raw data and/or reconstruction of physiological information from that raw data. Subsequently, these pre-computed transformation function components are used to expedite the computation of the full transformation functions. In circumstances where full reconstruction functions had been computed for particular locations of the catheter and/or electrodes 110, the computation of the forward transformation functions in real-time is avoided.

The pre-computed transformation functions can be used with any type of numerical computation methods used to solve the PDE's to obtain the reconstructed physiological information solutions. The following example illustrates how pre-computed transformation functions can be determined and used in conjunction with boundary element method (BEM) for solving the corresponding PDE's. It will be appreciated that similar mathematical frameworks can be developed for other numerical computation methods, and that generation of pre-computed transformation functions for use with those other numerical computation methods can likewise be performed.

The BEM method is based on Green's second identity, as provided below:

$$\int_S dS\left(U\frac{\partial V}{\partial n} - V\frac{\partial U}{\partial n}\right) = \int_\Omega d\Omega(U\nabla^2 V - V\nabla^2 U), \quad (1)$$

where V and U are two functions defined on the domain $\Omega$ with boundary S. The operator $\partial/\partial n$ is the normal derivative with respect to the outward normal and $\nabla^2$ is the Laplace operator (the so-called "Laplacian"). The above equation applies to an arbitrary domain, including domains with cavities. In the problem with a balloon catheter, $\Omega$ is the domain occupied by blood and S is the union of the (artificially closed-off) endocardium and the surface of the catheter.

The variable V represents the electrostatic potential, which has the property that its Laplacian vanishes. The variable U can be defined as $$U = \frac{1}{r}$$

with the distance r measured from a given origin o. The Laplacian of U can thus be represented as:

$$\nabla^2 \frac{1}{r} = -4\pi\delta_o(x, y, z), \quad (2)$$

where $\delta_o(x, y, z)$ is the three-dimensional Delta function at the origin o. Substituting the relationship represented in Equation (2) for U in Green's second identity, as shown in Equation (1), yields the following identity which is valid at all interior points of $\Omega$:

$$V = \frac{1}{4\pi} \int_S dS\left(\frac{1}{r}\frac{\partial V}{\partial n} - V\frac{\partial \frac{1}{r}}{\partial n}\right) \quad (3)$$

where r is the distance from the point at which V is being evaluated to each of the points on the surface. Similarly, the following relationship is valid for points on the boundary:

$$V = \frac{1}{2\pi} \int_S dS\left(\frac{1}{r}\frac{\partial V}{\partial n} - V\frac{\partial \frac{1}{r}}{\partial n}\right) \quad (4)$$

The variable $S_e$ is defined as the surface of the heart, and the variable $S_c$ is defined as the surface of the catheter. Thus, using this definition, the overall surface S, with respect to which equation (4) is to be solved, is defined as the union of the heart's surface and the catheter's surface, or $S = S_e \cup S_c$. Both surfaces are assumed closed and sufficiently smooth. Similarly, the variable $V_e$, and correspondingly $$\frac{\partial V_e}{\partial n}$$

are defined as the potential and its normal derivative on the surface of the heart. $V_c$ and $$\frac{\partial V_c}{\partial n}$$

are likewise defined as the potential and its normal derivative on the surface of the catheter. It will be appreciated that solving the PDE's with respect to surface potential is for illustrative purposes only, and that Green's second identity relationship may be solved for other types of physiological information.

In the forward problem, $V_e$ is subject to Dirichlet boundary conditions on $S_e$ and zero Neumann boundary conditions on $S_c$ in the case where the catheter displaces a significant amount of blood. Accordingly, $V_e$ and $V_c$ can be determined using the following pair of equations:

$$V_e = \frac{1}{2\pi}\int_{S_e} dS\left(\frac{1}{r}\frac{\partial V_e}{\partial n} - V_e \frac{\partial \frac{1}{r}}{\partial n}\right) + \frac{1}{2\pi}\int_{S_c} dS\left(\frac{1}{r}\frac{\partial V_c}{\partial n} - V_c \frac{\partial \frac{1}{r}}{\partial n}\right) \quad (5)$$

$$V_c = \frac{1}{2\pi}\int_{S_e} dS\left(\frac{1}{r}\frac{\partial V_e}{\partial n} - V_e \frac{\partial \frac{1}{r}}{\partial n}\right) + \frac{1}{2\pi}\int_{S_c} dS\left(\frac{1}{r}\frac{\partial V_c}{\partial n} - V_c \frac{\partial \frac{1}{r}}{\partial n}\right) \quad (6)$$

While Equations (5) and (6) appear identical, in each case the variable r is the distance from the point at which $V_e$ or $V_c$ is being evaluated to each point on either $S_c$ or $S_e$. In other words, the variable r assumes, for each of the equations, different values during the evaluation of the respective integrals, thus resulting in different values for $V_e$ and $V_c$. Since $$\frac{\partial V_c}{\partial n} = 0,$$

these equations simplify to $$V_e = \frac{1}{2\pi}\int_{S_e} dS\left(\frac{1}{r}\frac{\partial V_e}{\partial n} - V_e \frac{\partial \frac{1}{r}}{\partial n}\right) + \frac{1}{2\pi}\int_{S_c} dS\left(-V_c \frac{\partial \frac{1}{r}}{\partial n}\right) \quad (7)$$

$$V_c = \frac{1}{2\pi}\int_{S_e} dS\left(\frac{1}{r}\frac{\partial V_e}{\partial n} - V_e \frac{\partial \frac{1}{r}}{\partial n}\right) + \frac{1}{2\pi}\int_{S_c} dS\left(-V_c \frac{\partial \frac{1}{r}}{\partial n}\right) \quad (8)$$

Suppose that both surfaces are represented by irregular meshes and that $V_e$ and $V_c$ are now discrete BEM approximations to the true potential (or other physiological characteristics), subject to truncation errors as well as round off errors. The integration operation can be replaced by discrete operators $S_{e \to e}, O_{e \to e}, S_{c \to e}, O_{c \to e}, S_{e \to c}, O_{e \to c}, S_{c \to c}, O_{c \to c}$. Mnemonically, "S" stands for "Solid angle", "O" stands for "One-over-r" and the subscripts refer to either endocardium surface ("e") or the catheter surface ("c"). These discrete operators, which approximate the integration operation performed to determine the potentials at the respective surfaces can thus be represented as matrices. For a collocation-type BEM in which the potential is assumed to be constant over an entire element (e.g., a surface element on the particular representation of the surface used), the contribution from the operator $S_{e \to e}$ to the potential at the $i^{th}$ element of the endocardium surface based on the $j^{th}$ element on the endocardium surface can be computed as:

$$(S_{e \to e})_{ij} = -\frac{1}{2\pi}\int_{\Delta_j} \frac{\partial \frac{1}{r_{ij}}}{\partial n} dS, \quad (9a)$$

where the integration takes place over the $j^{th}$ element, and $r_{ij}$ is the distance from a given point on the $j^{th}$ element to the center of the $i^{th}$ element. Similarly, the other operators can be expressed as follows:

$$(O_{e \to e})_{ij} = \frac{1}{2\pi}\int_{\Delta_j} \frac{1}{r_{ij}} dS, \quad (9b),$$

where the $i^{th}$ and $j^{th}$ elements are both on the endocardium surface, $$(S_{c \to e})_{ij} = -\frac{1}{2\pi}\int_{\Delta_j} \frac{\partial \frac{1}{r_{ij}}}{\partial n} dS, \quad (9c),$$

$$(O_{c \to e})_{ij} = \frac{1}{2\pi}\int_{\Delta_j} \frac{1}{r_{ij}} dS, \quad (9d),$$

where the $i^{th}$ element is on the endocardium surface and the $j^{th}$ element is on the catheter surface, $$(S_{e\to c})_{ij} = -\frac{1}{2\pi}\int_{\Delta_j}\frac{\partial\frac{1}{r_{ij}}}{\partial n}dS, \quad (9e)$$

$$(O_{e\to c})_{ij} = \frac{1}{2\pi}\int_{\Delta_j}\frac{1}{r_{ij}}dS, \quad (9f)$$

where the $i^{th}$ element is on the catheter surface and the $j^{th}$ element is on the endocardium surface, and $$(S_{c\to c})_{ij} = -\frac{1}{2\pi}\int_{\Delta_j}\frac{\partial\frac{1}{r_{ij}}}{\partial n}dS, \quad (9g)$$

$$(O_{c\to c})_{ij} = \frac{1}{2\pi}\int_{\Delta_j}\frac{1}{r_{ij}}dS, \quad (9h)$$

where the $i^{th}$ and $j^{th}$ elements are both on the catheter surface,

The integral equations above can be converted into the finite linear system $$V_e = S_{e\to e}V_e + O_{e\to e}\frac{\partial V_e}{\partial n} + S_{c\to e}V_c \quad (10)$$

$$V_c = S_{e\to c}V_e + O_{e\to c}\frac{\partial V_e}{\partial n} + S_{c\to c}V_c \quad (11)$$

Combining like terms yields:

$$(S_{e\to e} - I)V_e + O_{e\to e}\frac{\partial V_e}{\partial n} + S_{c\to e}V_c = 0 \quad (12)$$

$$S_{e\to c}V_e + O_{e\to c}\frac{\partial V_e}{\partial n} + (S_{c\to c} - I)V_c = 0 \quad (13)$$

where I is the identity operator.

In the above system, for the forward transformation, $V_e$ is known while $$\frac{\partial V_e}{\partial n}$$

and $V_c$ are unknown. The system can be rewritten in block form as $$\begin{bmatrix} O_{e\to e} & S_{c\to e} \\ O_{e\to c} & S_{c\to c} - I \end{bmatrix}\begin{bmatrix} \frac{\partial V_e}{\partial n} \\ V_c \end{bmatrix} = \begin{bmatrix} (I - S_{e\to e})V_e \\ -S_{e\to c}V_e \end{bmatrix} \quad (14)$$

The vector $$\frac{\partial V_e}{\partial n}$$

can be eliminated from the above system, leaving the following expression for $V_c$:

$$V_c = (-S_{c\to c} + I + O_{e\to c}O_{e\to e}^{-1}S_{c\to e})^{-1}(O_{e\to c}O_{e\to e}^{-1}(I - S_{e\to e}) + S_{e\to c})V_e \quad (15)$$

The operators, or matrices, applied to $V_e$ form the so-called forward transformation, denoted A, that relates the potentials at the endocardium surface, resulting from the electrical activity of the heart, to the potential measured at the multiple electrodes of the catheter 110. In order to provide the transformation from catheter to endocardial potentials, we must interpret A as an equation for $\hat{V}_e$ given $V_c$. Because matrix A is generally rectangular, underdetermined, and rank deficient to within IEEE double precision, reconstructing $\hat{V}_e$ correctly through direct inversion is difficult because this equation allows infinitely many solutions, all but one of which are incorrect. Instead, some type of regularization technique is used to incorporate a priori knowledge about the system to better specify the correct solution. The regularization technique may include mathematical smoothing, statistical methods, and/or iterative techniques, such as conjugate gradient methods. Further below, a Tikhonov regularization technique is described for solving for $\hat{V}_e$; however, such a technique is by no means limiting.

With reference again to Equation (15), several of the matrices that form the forward transform A are pre-computed prior to the reconstruction operations. For example, the matrix $S_{c\to c}$ depends only on the geometry of the catheter and can therefore be pre-computed. If the catheter can assume different shapes and configurations, separate $S_{c\to c}$ matrices corresponding to each such shape/configuration are computed. The matrices $S_{e\to e}$, $O_{e\to e}$ and $O_{e\to e}^{-1}$ depend on the geometry of the heart and can be pre-computed if the shape of the heart is obtained before the procedure. In some embodiments $O_{e\to e}$ is the largest matrix since the heart is represented by a mesh with significantly more elements than the catheter. For example, the heart is typically represented by 3000 triangles while the catheter is typically represented by 500. Therefore, $O_{e\to e}$ is a 3000×3000 matrix, and thus its inversion would be costly (especially in terms of time) if the inversion had to be performed in real-time. The matrix computed as $-S_{c\to c} + I + O_{e\to c}O_{e\to e}^{-1}S_{c\to e}$, on the other hand, has a size of 500×500 elements and its inversion, therefore, could be performed more quickly.

The matrices corresponding to the independent geometry of the endocardium surface and/or the catheter are computed in advance of the signal acquisitions and/or reconstruction stages of the non-contact mapping. These pre-computed matrices are stored in a memory device, such as storage device 116 for later retrieval. After raw data had been acquired, the forward transform matrix is generated by retrieving, for example, the pre-computed $S_{e\to e}$, $O_{e\to e}$, and $O_{e\to e}^{-1}$ matrices, and using them in the course of computing the full forward transform matrix. In these embodiments where at least some of the pre-computed components associated with the forward transform are available, the forward transform matrix has effectively been partially pre-computed.

Unlike the matrices $S_{e\to e}$, $O_{e\to e}$, $O_{e\to e}^{-1}$ and $S_{c\to c}$, the other matrices depend on the configuration of the endocardium and the catheter 110 relative to each other (e.g., the relative distance between the catheter and specific locations on the endocardium surface). Although the relative positions and configuration of the endocardium surface relative to the catheter are typically known only when the catheter is inserted into the heart chamber and the data acquisition process has begun, to further expedite the reconstruction procedure, in some embodiments, the following matrix may be pre-computed for a large number of possible catheter locations:

$$(-S_{c \to e} + I + O_{e \to c} O_{e \to e}^{-1} S_{c \to e})^{-1} (O_{e \to c} O_{e \to e}^{-1} (I - S_{e \to e}) + S_{e \to c}) \quad (16)$$

Thus, for various discrete locations of the catheter 110 relative to the endocardium surface, the overall matrix expressed by Equation (16) can be independently computed and stored at storage device 160 (or elsewhere) for subsequent retrieval. During the performance of the mapping procedure, the catheter's position relative to the endocardium surface is determined and rather than computing the matrix of Equation (16) from scratch, the location is used to access a look-up table to retrieve the appropriate pre-computed matrix corresponding to the determined location.

The practicality of computing full forward transforms depends, to an extent, on the type of catheter used. For example, balloon-type catheters are configured in such a way that their movement in the heart chamber causes enough of the blood occupying the heart chamber to be displaced that a significant change in potential distribution occurs. As a result, for every variation of the position and orientation of a balloon-type catheter inside the heart chamber there will be a different forward transform associated with that position/orientation. The effort of pre-computing forward transforms for various positions/orientations of a balloon-type catheter then becomes proportional to the product of the number of possible spatial positions and the number of rotational configuration at those positions.

On the other hand, for some types of catheters, for example branch-shaped catheters (or otherwise porous, hollow catheters), the extent of blood displacement in the heart chamber is much less significant than for balloon-shaped catheters. Accordingly, one can approximate the presence of the catheter as having no effect on the electrostatic potentials inside the heart cavity, and essentially the integrations over the catheter surface in Equations (7) and (8), and the equations derived there from, can be ignored. As a result, the catheter orientation is no longer required to calculate the forward transform matrix A, the only knowledge that is required regarding the catheter is the positions of the various catheter electrodes.

For the type of catheters that do not displace a significant amount of blood the solution V to Laplace's equation at any interior point of $\Omega$ is given by $$V = \frac{1}{4\pi} \int_{S_e} dS \left( \frac{1}{r} \frac{\partial V_e}{\partial n} - V_e \frac{\partial \frac{1}{r}}{\partial n} \right)$$

where $V_e$ is specified by Dirichlet boundary conditions and $$\frac{\partial V_e}{\partial n}$$

is determined from the integral equation $$V_e = \frac{1}{2\pi} \int_{S_e} dS \left( \frac{1}{r} \frac{\partial V_e}{\partial n} - V_e \frac{\partial \frac{1}{r}}{\partial n} \right)$$

or, in the matrix form $$V_e = O_{e \to e} \frac{\partial V_e}{\partial n} + S_{e \to e} V_e$$

which means that $$\frac{\partial V_e}{\partial n}$$

can be computed from $V_e$ by only applying matrices $O_{e \to e}$ and $S_{e \to e}$ which can be entirely pre-computed:

$$\frac{\partial V_e}{\partial n} = O_{e \to e}^{-1} (I - S_{e \to e}) V_e$$

Importantly, this means that theoretically the forward operator can be pre-computed for finding the solution to Laplace's equation at any point in the interior of the heart. In reality, the forward operator needs to be pre-computed for a sufficient number of interior points so that an accurate solution at any interior point can be computed by a simple interpolation.

In general, for all types of catheters, significant benefits can be drawn from pre-computing the forward operator for a number of strategically selected catheter locations. When the physical catheter is found near a pre-computed location it is generally true (to the extent that the two configurations are indeed very similar) that the forward operator can be approximated by the pre-computed one. Therefore, benefits can be drawn both as far as efficiency and efficacy of regularization. For example, applying the pre-computed inverse to the observed electrode potentials will yield an excellent initial guess for iterative linear system solvers, significantly reducing the computation time. Further, an SVD-based low-rank approximation of the pre-computed operator A is likely to be a good preconditioner for the same iterative solvers further reducing the computation time. Finally, representing to endocardial potential in the right singular functions of the pre-computed operator A can be a very effective form of regularization and further diminish the required computation time by dramatically reducing the number of degrees of freedom from about 3000 to typically under 100.

In some embodiments, pre-computed matrices generated for select locations of the catheter may be used to estimate the matrices for other locations of the catheter 110 with respect to which corresponding forward matrices were not pre-computed. Perturbation analysis can be used to do this. For example, suppose that a satisfactory inverse operator has been constructed for a certain relative configuration of the endocardium and the catheter. Subsequently, the electrophysiologist moves the catheter by a small amount. A boundary perturbation technique can be used for reconstructing the potential on the endocardium by utilizing the measurements on the displaced catheter, the known amount of displacement, and the inverse operator constructed for the original position. For example, the matrix for the new location can be determine by using the pre-computed matrices for nearby locations, or components therein, as bases in a perturbative solution (e.g., a linear superposition of the basis functions or matrices) for determining the matrix for the new location.

In some embodiments, pre-computed transformation matrices may be generated for separate representations of the endocardium surface in circumstances where different representations for different phases of the heart's cycle are used. Thus, for each of those separate representation of the endocardium surface, corresponding pre-computed matrices are generated that are based on the individual geometry of these endocardium surface representations. Similarly, where several types of catheters may be used (or where a catheter may have different possible catheter configurations), the matrices which depend on the geometry of the catheter (e.g., $-S_{c \to c}$) may be individually generated for each of those catheters. During the reconstruction procedure, the matrices corresponding respectively to the chosen catheter and to the particular endocardium surface geometry are retrieved from storage device 160 and used to complete the computation of the full forward matrix corresponding to the particular location at which raw data was acquired.

Catheter Registration

As explained above, an important aspect of the non-contact mapping procedure is the determination of the catheter's position relative to the endocardium surface representation. The relative position of the catheter with respect to the endocardium surface representation is required, among other reasons, to compute the reconstruction transformation functions to compute the physiological information at the endocardium surface.

Figure 6:
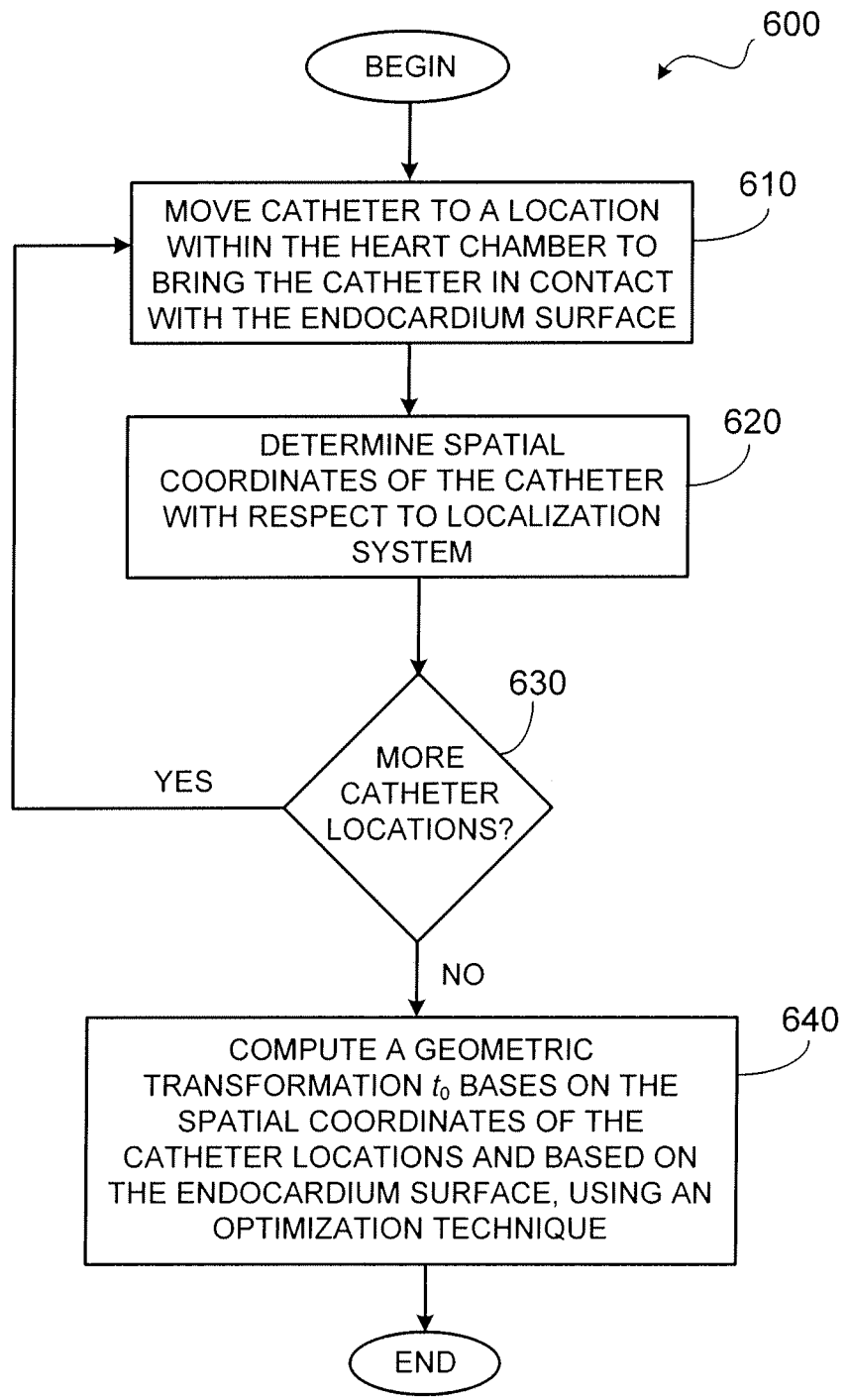
FIG. 6 is a flowchart of an exemplary embodiment of a catheter registration procedure.

FIG. 6 is a flowchart of an exemplary embodiment of a catheter registration procedure 600 for determining a transformation function that aligns the catheter's coordinate system with the coordinate system of the endocardium surface representation, and thus enables expressing the position of the catheter's location in terms of the endocardium surface's coordinates system. The following will describe two methods for performing catheter registration. The first method relates to a point cloud to surface registration while the second method employs the identification of fiduciary anatomical markers.

FIG. 6 describes a point cloud to surface registration. As shown in FIG. 6, a catheter is first inserted into the heart chamber and is moved to a location where the catheter and/or at least one of its electrodes touch the endocardium surface (at 610). In some embodiments an operator moves the catheter 110 inside the heart chamber until it determines that the catheter, or one or more of its electrodes, touches the endocardium surface. In determining whether the catheter 110 or any of its electrodes are touching the walls of the endocardium surface, the operator may be guided by visual aides such as a real-time ultrasound system providing a visual image of the catheter inside the heart chamber, a camera coupled to a fibreoptic strand connected to the catheter, fluoroscopy, impedance measurements, the size and shape of intracardiac electrograms, pressure sensors fitted on the tip of the catheter etc. Additionally, the operator may determine that the catheter is touching the endocardium surface when it encounters the higher mechanical resistance exerted by the endocardium walls, thereby alerting the operator that the catheter is at the endocardium surface. In yet further embodiments, a catheter may be guided to the endocardium walls automatically with minimal intervention from the operator.

Once the catheter has been placed in a location abutting the endocardium surface, the 3D spatial coordinates of the catheter (and/or its electrodes) is determined at 620. The spatial coordinates may be established using one of several conventional sensing and tracking systems. Such conventional sensing and tracking systems (also referred to as localization systems) include systems that determine the location of the tracked object (in this case the catheter and/or its electrodes) using magnetic fields, electric fields, fluoroscopy, and ultrasound signals. These systems localize the catheter in the 3D space of the localization system.

See, for example, any of U.S. Pat. Nos. 5,697,377 entitled "Catheter mapping system and method," 5,983,126 entitled "Catheter location system and method," 6,690,936 entitled "System for determining the location and orientation of an invasive medical instrument," 5,713,946 entitled "Apparatus and method for intrabody mapping," 5,694,945 entitled "Apparatus and method for intrabody mapping," 5,568,809 entitled "Apparatus and method for intrabody mapping," 5,833,608 entitled "Magnetic determination of position and orientation," 5,752,513 entitled "Method and apparatus for determining position of object," and 6,427,314 entitled "Magnetic determination of position and orientation," and U.S. Patent Application Publication entitled "Method and apparatus for catheter navigation and location and mapping in the heart."

As noted above, in some embodiments, the location of the electrodes relative to the catheter 110 is fixed and known, and thus the only information that needs to be determined is the location and orientation of the catheter 110 in the 3D space established by the localization system. In other embodiments, the location of the various electrodes relative to the catheter may vary, and accordingly in such embodiments electrodes may be tracked individually relative to the endocardium, or relative to a location on the catheter with known position relative to the endocardium. Electrode tracking may employ any of the above mentioned tracking methods such that instead of tracking only one known point on the catheter, each electrode is individually tracked.

At 630 it is determined if additional catheter locations are required to perform the registration procedure. A minimum of three (3) separate catheter locations are required to obtain an accurate geometric transformation between the catheter's coordinate system and the endocardium's surface representation's coordinate system. However, to improve the accuracy and reliability of the coordinate system transformation, more catheter locations could be used.

If additional locations are required, the procedure depicted at 610-620 is repeated. Particularly, the operator moves the catheter 110 to the next point on the endocardium surface, and the 3D coordinates of the catheter 110 relative to the localization system are determined.

Subsequently, after N locations of the catheter 110 at the endocardium surface have been acquired, and their 3D spatial coordinates relative to the localization system determined, the registration transformation, $t_0$, is computed at 640. As described above, to map the localization system's coordinate system to the endocardium surface representation's coordinate system, the computed geometric transformation is the one that best matches the 3D locations of the catheter 110, as determined at 610-630, to the endocardium surface representation.

In some embodiments, computation of the registration transformation $t_0$ is performed by minimizing the following expression:

$$\min_{t_0} \sum_{i=1}^{N} d_i^2 \qquad (17)$$

To perform the minimization of Equation (17), the surface S, representing the segmented boundary of the endocardium surface and nearby vessels, is defined. Also defined are the vector $p_i$, which corresponds to the 3D spatial coordinates measured for the roving catheter using the localization system, and the operator $T[t_0](p_i)$ which is the transformation operator performed on the points $p_i$. The resultant vector $t_0$ is represented as a six parameter transformation $[x_0, y_0, z_0, \theta_0, \phi_0, \psi_0]$ that is applied to catheter locations to express those locations in terms of the endocardium surface coordinate system.

The distance function D is defined such that $d_i = D(T[t_0](p_i), S)$ represents the distance from transformed point $T[t_0](p_i)$ to the surface S. To determine the vector $t_0$ with respect to which the term $d_i$ for the acquired N catheter locations on the endocardium surface is minimized, a number of techniques may be used, including conventional iterative optimization techniques such as least-square error computation procedures and/or other mathematical regression and curve-fitting techniques.

In other embodiments, determination of the transformation vector $t_0$ may be achieved using the fiduciary anatomical markers technique. In this technique, a number of fiduciary markers are identified in both the endocardial boundary and the localization system respective coordinate systems. Once identified, the transformation that yields the minimum mean square error between the two point sets is chosen.

For example, anatomical landmarks that are easy to identify in both modalities (Mitral annulus, coronary sinus, etc.) are used as the fiduciary markers. These landmarks may be easily identified in the pre-acquired endocardial boundary. Once a given landmark is identified, the catheter may be advanced to the landmark guided, for example, by fluoroscopy. Once in contact, a reading from the catheter localization system is taken to establish the catheter's position in terms of localization system's coordinate system.

A variation of the above technique may be to place surface markers on the patient that are easy to identify in both the pre-acquired and real-time localization modalities.

The registration process yields a transformation vector that includes three (3) displacement parameters $(x_0, y_0, z_0)$ and three rotation parameters $(\theta_0, \phi_0, \psi_0)$. This transformation can then be applied to 3D spatial coordinates obtained by the localization system to obtain the roving catheter's location in terms of the endocardium surface representation's coordinate system. The mapped locations of the catheter's 110 are subsequently used to compute the reconstruction transformation, and/or perform all other computations that require the catheter's location in terms of the endocardium surface's coordinate system.

It is to be noted that for a healthy patient in sinus rhythm the endocardial boundary is relatively fixed throughout the propagation of the activation wavefront. This implies that a small error tolerance is available when basing the registration process on a single boundary shape for the construction of the geometrical mapping between the localization system and endocardial surface representation respective coordinate systems.

In some cases changes in blood volume between the time of image acquisition and the time of registration or the presence of a persistent arrhythmia may lead to a change in chamber volume, and therefore a mismatch between the preacquired and current endocardial surface. Such mismatch leads to error when performing reconstruction of physiological signal on the endocardial surface. Volume changes are generally lower than 20%. A number of methods may be used to compensate for this volume change. One method is to add a scaling parameter that uniformly dilates or contracts the endocardial representation relative to the acquired point cloud. When performing the abovementioned minimization of equation (17) a scaling parameter $S_0$ may be added to the transformation vector. Rather than optimizing for 6 parameters, the minimization algorithm optimizes for 7 parameters providing the scaling factor which is expected to be in the range of ±20%. Other, more elaborate methods, may also scale the endocardial surface non-uniformly such that anatomical areas that are a-priory known to be less likely to experience a change in shape due to volume changes are scaled less than those more likely to change.

In case of persistent arrhythmia the heart may experience mechanical change during the activation wavefront propagation. As discussed previously, it is possible to obtain endocardium boundary representation for multiple phases of the mechanical cycle. Thus, in some embodiments several geometrical transformation vectors, such as $t_0$, corresponding to multiple heart shapes may be computed. The system may detect physiological data such as ECG, intracardiac electrograms and stroke volume using impedance plethysmography and use this data to select the cardiac phase, appropriate endocardial boundary representation and the corresponding geometric transformation $t_0$.

It will be appreciated that while the transformation $t_0$ establishes the geometric mapping with a respect to a representative point on the catheter 110 (e.g., the tip of the electrode that touched the endocardium surface when the catheter was moved around, the central point on the body of the catheter, etc.), the coordinates of any point on the catheter and/or its electrode in terms of the endocardium surface representation's coordinate system can be determined.

Reconstruction of Physiological Information at the Endocardium Surface

Given the relative location of the catheter and/or its electrodes to the endocardial boundary, the numerical transformation from the signals measured by the electrodes to the physiological information (e.g., electrical potentials) at the endocardial surface can be computed.

The physical laws governing the reconstruction of the physiological information at the endocardium surface are briefly summarized below:

The potential V in a homogeneous volume $\Omega$ is governed by Laplace's equation $$\nabla^2 V = 0 \qquad (18)$$

subject to boundary conditions $$V = V_e, \text{ on the surface } S_e \qquad (19)$$

$$\frac{\partial V}{\partial n} = 0, \text{ on the surface } S_c,$$

where $S_c$ is catheter surface and the vanishing normal derivative accounts for the fact that the current does not penetrate $S_c$. Se represents the endocardial surface. In case of a branch-shaped catheters (or otherwise porous, hollow catheters), where the extent of blood displacement in the heart chamber is much less significant than for balloon-shaped catheters, the constraint of vanishing normal derivative may be omitted.

As previously alluded to, with the exception of a handful of geometries, Laplace's equation needs to be solved numerically. Numerical methods such as boundary element method (BEM), finite element method (FEM), finite volume method, etc. may be used to solve Laplace's equation. For some special geometries, such as near-spherical geometries, spherical harmonics may be used. Each numerical method represents the geometry in a discrete way, but each method uses its own representation. In all numerical methods the potentials on the endocardial surface and on the catheter are represented by finite-dimensional vectors. Since Laplace's equations are linear, these vectors are related by a matrix A, known as the forward matrix:

$$V_c = AV_e \qquad (20)$$

where $V_c$ is a vector containing the potentials measured by the electrodes on the catheter and $V_e$ is a vector containing the real endocardial potentials. The matrix A has dimensions of m×n, where m is the number of electrodes on the catheter and n is the number of degrees of freedom in the endocardial potential, usually the number of surface elements used to represent the surface $S_e$. Typically m<n. However, as noted, by moving the catheter around the heart chamber and subsequently computing a reconstruction transformation that is applied to a composite of the raw data corresponding to the signal acquired at the multiple locations, the effective number of electrodes m can be increased, thereby reducing the disparity between m and n and thus improving the accuracy of the computations.

Equation (20) provides a transformation relationship from the endocardial to the catheter potentials. This relationship, which is generally referred to as the forward problem, is well posed and can be solved with great precision. To provide the transformation from catheter to endocardial potentials, $\hat{V}_e$, a vector representing the estimated endocardial potentials, has to be determined given $V_c$. Since matrix A is generally rectangular, underdetermined, and rank deficient to within IEEE double precision, solving this equation is difficult, if not impossible.

The first step towards calculating $\hat{V}_e$ is to reformulate Equation (20) as a least squares problem in which the expression $$\|V_c - A \times \hat{V}_e\|^2 \qquad (21)$$

also referred to as the objective function is minimized over all possible $\hat{V}_e$. The matrix A is either determined in real-time, or, as described above, a pre-computed matrix A corresponding to the particular geometry of the catheter 110 (including the position and orientation of the catheter) is retrieved from storage device 160. As also described above, if the storage device does not store full-forward transformation matrices A corresponding, for example, to the particular position(s) and/or orientation(s) of the catheter 110, the computation of the matrix A can nevertheless be expedited by retrieving from storage device 160 partially pre-computed functions or function components, and completing the computation of the matrix A as described with reference to Equation (16).

If A were over-determined (i.e., its rank exceeding the dimension of $V_c$), and typically it is not, then $\hat{V}_e$ could in theory be determined by the classical least squares formula:

$$\hat{V}_e = (A^T A)^{-1} A V_c \qquad (22)$$

However, because A is generally undetermined and, as a result, $A^T A$ is singular and cannot be inverted, the expression in Equation (22) cannot usually be applied in practice.

One difficulty relating to performing a least-square error procedure is that because the matrix A attenuates the physiological signal, the inverse operation needs to amplify the signal. The level of attenuation in the forward and amplification in the inverse depends on the size and the location of the catheter and the nature of the electrical potential on the endocardium.

In practice, significant components of $V_e$ are attenuated on the order of 1000 or greater. As a result, small errors in $V_c$ will produce large errors in $\hat{V}_e$. Thus the inverse problem is ill-posed.

A regularization technique can be used for dealing with the ill-posed nature of the inverse problem. The regularization technique involves making additional assumptions about the behavior of the endocardial signal. These assumptions may relate to the spatial or temporal characteristics of the physiological information at the endocardium surface.

One technique that can be used is the zeroth ($0^{th}$) order Tikhonov regularization technique. The technique is predicated on the assumption that the essential part of the signal is contained among the right singular values of A that correspond to the lowest singular values. An alternative geometric interpretation is that Tikhonov regularization limits the amplitude of spatial variation of the reconstructed signal. The zeroth order Tikhonov regularization results when a term that penalizes large endocardial potentials is added to the objective function. Thus, the least square error problem defined in Equation (21) can be re-formulated as:

$$\|V_c - A \times \hat{V}_e\|^2 + t\|\hat{V}_e\|^2 \qquad (23)$$

Where a minimization is performed over all possible $\hat{V}_e$. Solving this minimization yields the expression $$\hat{V}_e = (A^T A + tI)^{-1} A V_c$$

The regularization parameter t controls the amount of spatial smoothing applied to reconstructed potentials $\hat{V}_e$. The regularization parameter t provides a tradeoff between spatial resolution and sensitivity to noise. As t decreases, the reconstruction resolution is improved, but noise and the instability of the solution increases. In some embodiments, t may be chosen such that it is three (3) times the root mean square value of noise detected by the electrodes. Other methods such L-curve may be used to find an optimal regularization parameter.

In addition to addressing the ill-posedness of the inversion problem, Tikhonov regularization also solves the problem of the under-determination of A.

Figure 7:
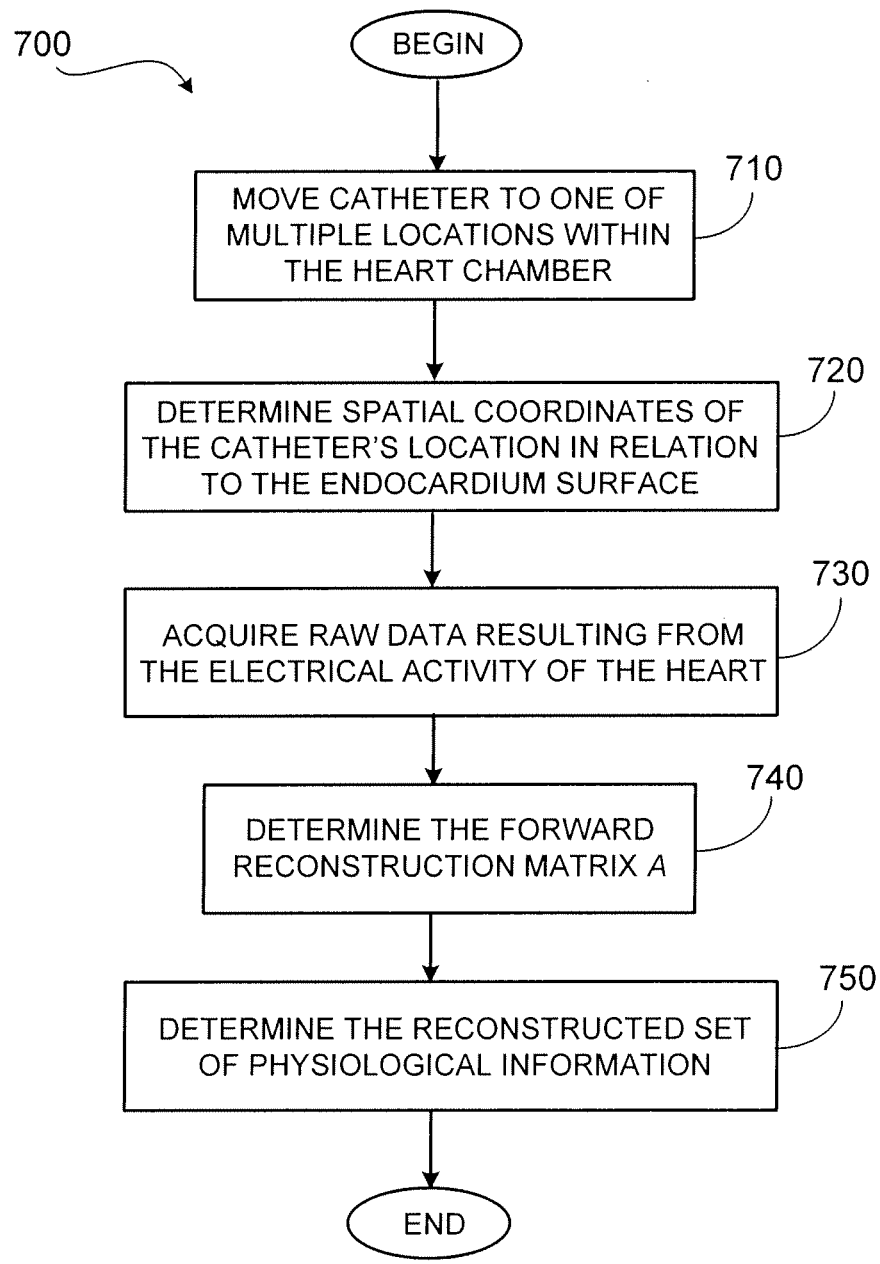
FIG. 7 is a flowchart of an exemplary embodiment of a procedure for reconstructing physiological information from signals acquired by the multiple electrodes of a catheter.

FIG. 7 is a flowchart of an exemplary procedure 700 for reconstructing physiological information from signals acquired by the multiple electrodes of the catheter 110.

As shown, the catheter 110 is moved to one of multiple locations within the heart chamber at 710. In some embodiments an operator controls the movement of the catheter and decides its next location, while in other embodiments the catheter's movement is fully or partially automated.

Once the catheter has reached a location in the heart chamber, the position of the catheter 110 in relation to the endocardium surface representation is determined at 720. Particularly, the localization system tracking the location of the catheter 110 determines the 3D spatial coordinates of the catheter 110 relative to the localization system. The localization system thus provides the position and orientation of the catheter 110 in tennis of the localization system coordinate system. The previously determined geometric coordinate transformation vector $t_0$ is then applied to the position of the catheter 110, as expressed in Willis of the localization system's coordinate system, and transforms that position to a resultant catheter position expressed in term of the endocardium surface's coordinate system.

The catheter's multiple electrodes then acquire the raw data signals that resulted from the electrical activity of the heart and send the signals to the processing unit 120 at 730. In some embodiments the acquired signals are electrical and/or magnetic signals resulting from the electrical activity of the heart. As will become apparent below, to reduce the error associated with the measurement of the signals, in some embodiments, the catheter's multiple electrodes acquire multiple sets of signal in each heart beat over several heart beats.

Additionally, in some embodiments signal acquisition is performed in several locations in the heart chamber. Under these circumstances the multiple sets of signals are processed (e.g., by performing an averaging or a weighted averaging operation) to generate a resultant set of raw data on which the reconstruction procedure will subsequently be performed. A forward transform A is then constructed for the composite raw data set that includes data from multiple catheter locations, and the reconstruction set of physiological data, corresponding to the composite set, is then determined. To consolidate the signals from the catheter's various locations into a composite set, a synchronization mechanism may be used to enable the system 100 to acquire signals at substantially the same cycle of heart's electrical activity. The synchronization could be based on physiological data (e.g., ECG measurements, intracardiac electrogram measurement, operator pacing) collected by the synchronization mechanism. Accordingly, the reconstruction of physiological information from a composite set obtained in the above-described manner results in processing the synchronized raw data signals as though they were obtained at one time from all the positions sampled by the catheter's electrodes for the different positions of the catheter in the heart chamber.

Having acquired the raw data, the forward reconstruction transform A is determined at 740. As explained above, the forward transform A depends on the position and/or orientation of the catheter 110 relative to the endocardium surface representation. In some embodiments, determining the matrix A includes computing the values of the forward matrix in accordance with the expression $(-S_{c \to c}+I+O_{e \to c} O_{e \to e}^{-1} S_{c \to e})^{-1}(O_{e \to c}O_{e \to e}^{-1}(I-S_{e \to e})+S_{e \to c})$, as more particularly explained above. In those embodiments where an actual computation of the above expression is carried out in real-time or near real-time, the computation is expedited by retrieving from storage device 160 (or some other memory device) pre-computed reconstruction matrix components such as the components relating to $S_{e \to e}$, $O_{e \to e}$, and $O_{e \to e}^{-1}$. Under these circumstances, the task of computing the forward transform A for a particular set of raw data is reduced to completing the computation of an already existing partially computed forward transform A by generating the missing components based on, for example, the particular position and orientation of the catheter 110.

In other embodiments, fully computed forward matrices, each corresponding to a particular position of the catheter, can be retrieved from storage device 160. In those embodiments the position of the catheter 110 and/or its electrodes is used to access a look-up table that maintains the various pre-computed forward transforms.

Having determined the forward transform, the reconstructed set of physiological information (e.g., electrical potentials) at the endocardium surface representation is determined at 750. In particular, a regularized inversion procedure as described above is used to estimate the values of the reconstructed physiological information set based on the set of raw data that was acquired (be it a set of data acquired from a single measurement by the multiple electrodes or some resultant set derived from multiple measurements) and the forward transform A that was determined at 750 (for example, as described above with respect to Equation (21)).

Once the reconstructed set of physiological information has been computed, the physiological information can be overlaid on the endocardium surface representation using, for example, conventional graphic display techniques (e.g., graphical rendering). Post-processing operations may be additionally applied to the set of reconstructed physiological information. The physiological information can be displayed, for example, using a color code whereby a color is assigned to ranges of values. A certain value corresponding to a particular surface element is mapped to a corresponding color which is then used to fill the area on the graphical representation of the endocardium associated with the surface element with that color. Other ways to represent the values of the physiological information can be used.

Signal Acquisition Over Multiple Heart Beats

As described herein, the reconstruction of physiological information at the endocardium surface is affected by noise. To control the effect noise has on the reconstructed information at the endocardium surface representation, the Tikhonov regularization technique can be used, whereby the regularization parameter t is chosen, in some embodiments, to be three times the root mean square of noise. Although the Tikhonov regularization technique helps to reduce the computation error due to noise, the technique adversely affects the spatial resolution of the reconstructed information. The larger the regularization parameter, the more spatially smooth (and hence low resolution) the reconstruction becomes. It is therefore preferable to reduce all sources of error when performing the reconstruction. The signals detected by catheter electrodes should be shielded to reduce interference and conditioned by a low noise input stage.

In addition to these measures, it is also possible to improve signal to noise by conducting measurements over a period of multiple heart beats. The signal to noise ratio can be improved by a factor of $\sqrt{B}$ where B is the number of measurements in the presence of a periodic signal and independent and identically distributed noise. Thus, in situations involving periodic arrhythmias, under the assumption that multiple beats are identical, it is possible to improve signal-to-noise ratio by sampling over multiple beats.

In situations where the catheter 110 maintains a fixed location, the forward transformation A remains constant between beats. The vector $V_c(t)$ is defined as the measurements made on the catheter at instant t. If the signals are sampled at increments of $\Delta t$ (e.g. 1 mS), then for a heart beat having a period P (e.g. 750 mS for 80 beats per minute) the measured signals can be expressed as $V_c(s \cdot \Delta t + P_b)$ or $V_c(s,b)$ where s is the phase number in the cycle, and $P_b$ is the time stamp at which the fiducial marker associated with beat b was detected. The parameter s can thus be regarded as a specific phase in the cardiac cycle. To assign a measurement at time t with the appropriate values of s and b, a specific fiducial marker needs to be identified within each heart beat. This can be done by relying on reference signals such as body surface ECG or intracardiac signals such as those collected in the coronary sinus. A specific implementation of this is described further below in the next section.

If data over a number of beats equal to B is collected, then B measurements of signals are available for the phase s of the heart cycle. Thus, the B measurements at the same phase can be averaged according to:

$$\overline{V}_c(s) = \frac{1}{B}\sum_{b=1}^{B} V_c(s, b) \quad (24)$$

Since the resultant set of signals corresponds to data averaged over B measurements, assuming independently and identically distributed noise sources an improvement in signal to noise proportional to $\sqrt{B}$ is obtained. The resultant averaged set of signal values are now used to perform the reconstruction of the physiological information, and accordingly the reconstruction resolution can be increased by using the averaged data and reducing the value of the Tikhonov regularization parameter t by a factor of $\sqrt{B}$.

Additional improvement in reconstruction accuracy can be obtained by moving the catheter. Since catheter movement is slow relative to the heart rate, when moving the catheter raw signals are acquired at multiple locations over multiple beats. Catheter movement and the use of multiple beats have several advantages. One advantage is that use of multiple beats improves the signal-to-noise ratio. Another advantage is that the movement of the catheter allows improved resolution in areas that the catheter was moved closer to, and effectively provides signal measurements from more electrode locations (thereby effectively providing more electrodes).

Unlike the fixed position catheter scenario, however, when the catheter acquires its measurements at multiple locations, the forward transform matrix A does not remain constant.

Generally, each catheter location where raw data is acquired would be associated with a corresponding forward transformation $A_b$. After collecting data over multiple beats in multiple locations and detecting the phase s for each measurement, a new measurement vector $V_c$ can be assembled that contains all electrode measurements conducted at the same (or substantially the same) phase s. Thus, the vector $V_c(s)$ can be expressed as:

$$V_c(s) = \begin{matrix} V_c(s, 1) \\ V_c(s, 2) \\ \vdots \\ V_c(s, B) \end{matrix} \qquad (25)$$

Additionally, a composite forward transform $\tilde{A}$ is defined such that:

$$\tilde{A} = \begin{matrix} A_1 \\ A_2 \\ \vdots \\ A_B \end{matrix} \qquad (26)$$

where $A_b$ are determined as described above.

The relationship between the composite vector $V_c(s)$, the composite forward transform $\tilde{A}$ and the reconstructed set of physiological information (in this case, electrical potentials) is expressed as:

$$\tilde{A} \cdot V_e(s) = V_c(s) \qquad (27)$$

Using the relationship articulated in Equation (27), the values of $V_e(s)$ (i.e., the reconstructed set of physiological information corresponding to a particular phase s) can be determined by performing the inverse procedure previously discussed. For example, a regularized inversion of $\tilde{A}$ may take place as discussed above.

The effect of moving the catheter for a periodic arrhythmia is similar to the effect of having multiple catheters in a single beat.

Until now it was assumed that the signal propagation is periodic, and that therefore $V_e(s,b_1)=V_e(s,b_2)$ for any $b_1$ and $b_2$. However, if the cardiac propagation is non-periodic, this assumption is not necessarily valid, and therefore an averaging operation to improve, for example, the signal-to-noise ratio, may not be feasible.

Nonetheless, even in situations involving non-periodic signals, there are several properties that remain substantially the same over multiple beats. For example, tissue properties remain relatively unchanged over a period of several minutes. One way to characterizing tissue is through the formation of a voltage map (as will be described below). Under the assumption that the maximum voltage amplitude in a particular area remains substantially constant over a period of multiple beats, a multi-beat enhancement of the voltage map resolution can be achieved. Particularly, the voltage map value can be defined as:

$$VMV = \max_s(\hat{V}_e(s)) - \min_s(\hat{V}_e(s)) \qquad (28)$$

As data is collected over B beats and a reconstruction operation is performed for each beat, B voltage maps $VMV_b$ are produced.

Let us suppose that we would like to find the VMV for a particular point on the endocardium for which we know both the voltage map values for each beat ($VMV_b$) and the reconstruction resolution for each measurement $Res_b$ (derived in a manner described below). We may now assign a new weighted average value for this VMV where $$\overline{VMV} = \frac{1}{\sum_{b=1}^{B} \beta_b} \cdot \sum_{b=1}^{B} \beta_b \cdot VMV_b \qquad (29)$$

where $$\beta_b = \frac{1}{Res_b}.$$

It will be appreciated that other types of averaging schemes to determine the average VMV may be utilized.

Signal Phase Alignment

Figure 12:
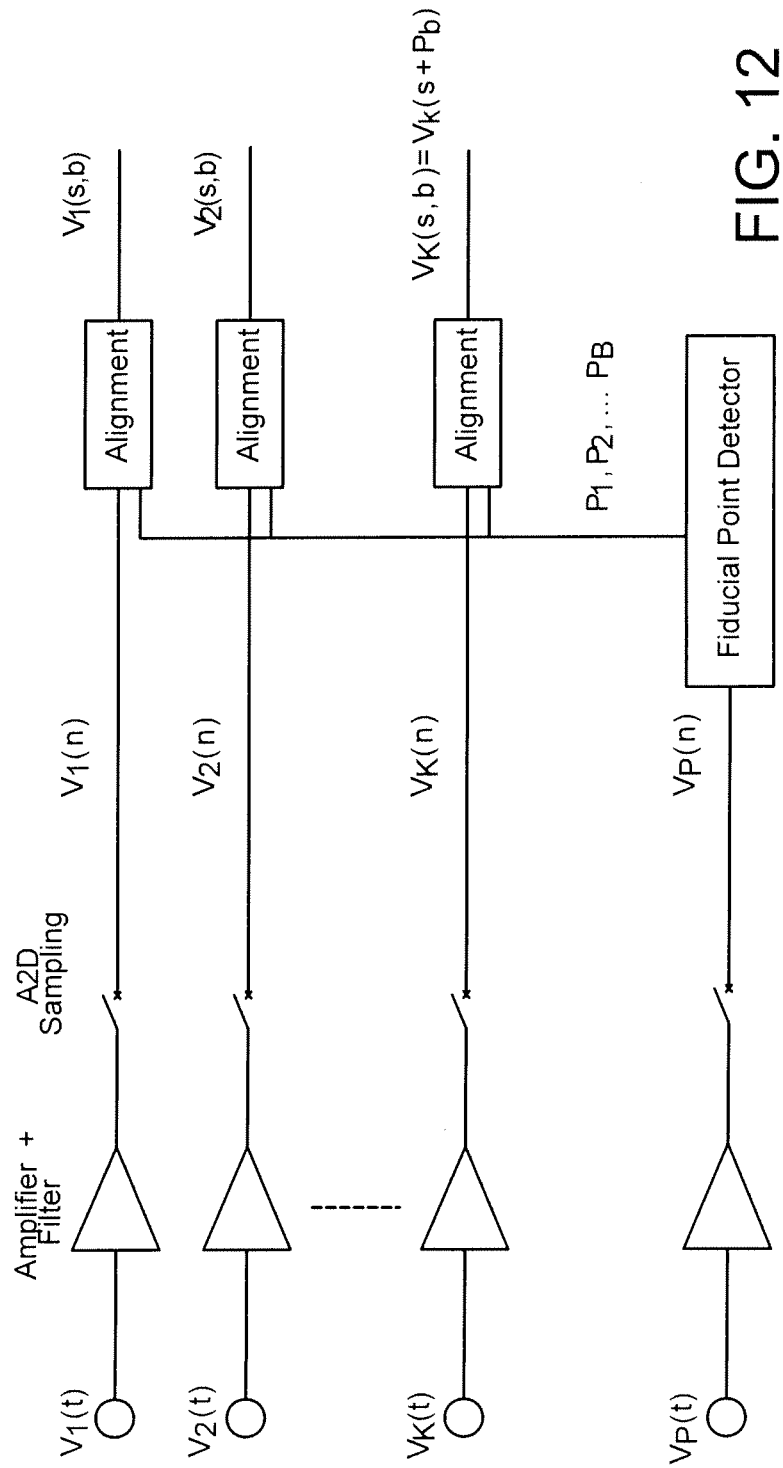
FIG. 12 is a schematic diagram showing signal phase alignment.

In order to process data acquired over multiple beats it is necessary to align the data relative to a specific phase in the electrical cycle. The following describes a method of aligning the K signals $V_1(t)$-$V_K(t)$, as shown in FIG. 12.

In the first stage, all signals are amplified, filtered and sampled. A synchronization signal is concurrently acquired in an identical manner. The synchronization signal can be acquired from surface ECG, or an intracardiac signal in a fixed location such as that detected by a coronary sinus catheter.

The Fiducial Point Detector (FPD) detects the time markers at which particular event occur. For example, the FPD may detect the R wave in surface ECG or activation time of an intracardiac electrogram. The detection is performed in a manner similar to alignment methods for averaging of high resolution ECG. See, for example, Jane Raimon, "Alignment methods for averaging of high resolution cardiac signals", *IEEE Transactions in Biomedical Engineering*, Vol. 38 No. 6 (June 1991); Brooks, Dana, "Improved alignment method for noisy high-resolution ECG and Holter records using multi-scale cross-correlation", *IEEE Transactions in Biomedical Engineering*, Vol. 50, No. 3 (March 2003); Breithardt, Gunter, "Standards for analysis of ventricular late potentials using high-resolution or signal-averaged electrocardiography", *Circulation*, Vol. 83, No 4 (April 1991).

Briefly, a template signal is cross-correlated with the synchronization signal. Fiducial points are detected when the cross-correlation between the template and synchronization signal reach a maximum. The template signal itself may be a relatively clean signal that was acquired from the synchronization signal previously, or an average of a number of these signals. The template signal may be selected visually by the user or automatically by a computer algorithm which uses a priori knowledge about the statistics of the signal.

It should be noted that in case of mapping performed during pacing, the synchronization signal may come from the pacing apparatus. In this case, no cross-correlation is necessary and the FPM will just pass the time markers associated with the synchronization signal.

The FDM outputs the time markers $P_1 \ldots P_B$ at which the fiducial points were detected. These time markers are then used to align the acquired signals. After the acquired signals are aligned, they are expressed as $V_K(s,b)$, where s is the phase number in a particular beat b.

Post Processing and Visualization

A number of post-processing and visualization techniques may be used to display the reconstructed physiological information in a clinically meaningful manner. Some of the post-processing operations include the following.

A. Resolution Display

As discussed previously, the potential is greatly attenuated on its way from the endocardial surface to catheter electrodes. The potential may be attenuated so much, that by the time it reaches the catheter its values are lower than the noise floor. Due to this attenuation, potentials (or other types of physiological information) on the endocardium surface representation in areas that are closer to the catheter may be reconstructed with greater accuracy and spatial resolution than potentials in areas farther away from the catheter. To increase the utility of reconstructed potentials such that clinical decisions can be aided by the information they provide, it is useful to provide the physician with information about the fidelity of the reconstruction.

In some embodiments a heuristic approach that is designed to measure how much of the signal remains above noise by the time it reaches to the catheter is used to compute resolution maps. Generally, signals experience attenuation which depends, among other things, on the spatial frequency of signal. That is, the higher the spatial frequency, the greater the level of attenuation.

The singular value decomposition of the forward transform A suggests an approach for determining the attenuation levels of the forward transformation. Particularly, in the singular value decomposition of A, the right and left singular vectors $R_i$ and $L_i$ are unique orthonormal bases that map one to another under A and are related through the vector $\sigma_i$ which represents an attenuation of one basis, relative to the other. Thus, decomposing the endocardial signal $V_e$ under A with respect to the right singular vectors of A provides:

$$V_e = \sum_i \alpha_i R_i \quad (30)$$

Accordingly:

$$V_c = AV_e = \sum_i \alpha_i \sigma_i L_i \quad (31)$$

It follows that the portion of the signal proportional to the singular vector $R_i$ is "reconstructible" if $\alpha_i \sigma_i$ exceeds the level of noise. In some embodiments, an endocardial signal $V_e$ is deemed to be reconstructible if the singular value components that remain above noise after being transformed by A add up to at least 60% of the total signal energy. The resolution at a particular point i on the endocardium is said to be $Res_i$ if a bell-shaped signal centered at that point and having a "standard deviation" of $Res_i$ is reconstructible.

Another approach to determine the resolution of the reconstructed physiological information at the endocardium surface representation also relies on the use of the forward transform A. As was explained, A is a matrix of size m×n where the number of rows in corresponds to the number of catheter electrodes and the number of columns n is the number of elements on the mesh describing the shape of the endocardium surface. For example, the values in column i in A can represent the voltage measurements on all electrodes had there been a potential of 1V on the $i^{th}$ element on the mesh and a potential of 0V everywhere else. Therefore, summing the squared values in a particular column i and dividing the sum by the number of electrodes, yields a value proportional to the average amount of energy that propagated from element i on the heart surface to the catheter's electrodes. Thus, the resolution $Res_i$ for the $i^{th}$ element on the endocardium surface can be expressed as:

$$Res_i = \frac{1}{m} \sum_{j=1}^{m} A_{j,i}^2 \quad (32)$$

It will be appreciated that each squared entry in the column corresponds to the energy received by one of the catheter electrodes (j in the above equation represents the $j^{th}$ electrode of the catheter).

The average amount of energy that makes it from a particular element i on the heart's surface to the catheter's electrodes is a good indicator of the reconstruction resolution. Areas on the heart surface whose voltage is attenuated greatly by the time they reach the catheter are reconstructed with poor resolution while areas whose voltage arrives less attenuated are reconstructed more accurately.

In general, reconstruction resolution on a particular point on the endocardial boundary depends on that point's distance to the catheter and the solid angle at which the catheter appears from that point.

Figure 8:
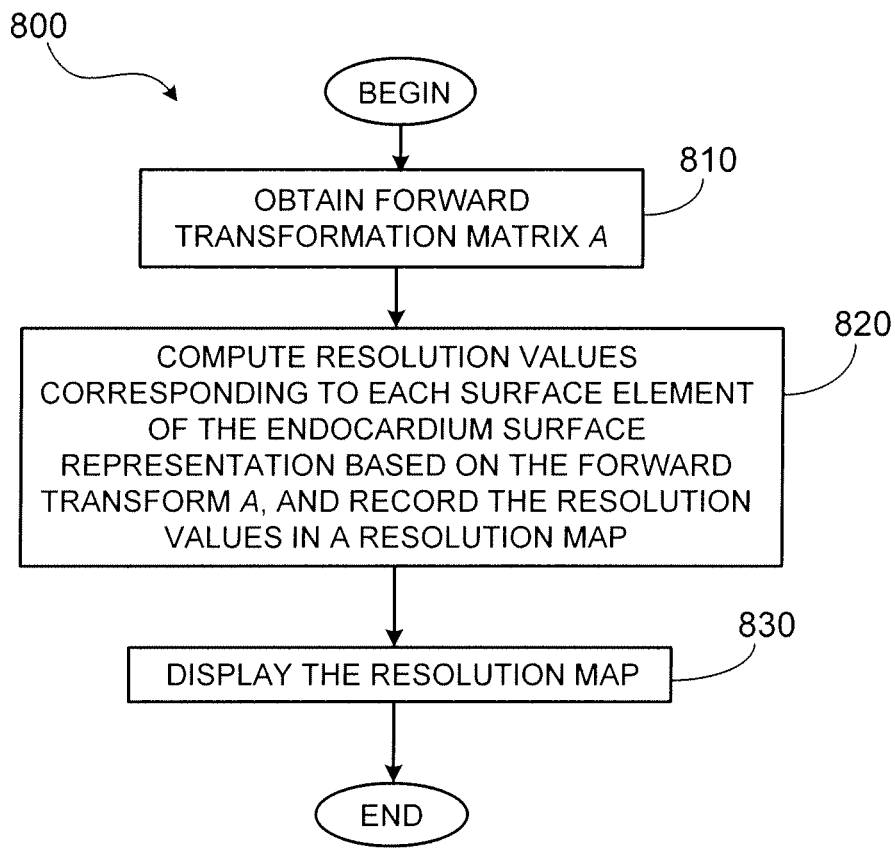
FIG. 8 is a flowchart of an exemplary embodiment of a procedure to generate a resolution map.

FIG. 8 is a flowchart of an exemplary embodiment of a procedure 800 to generate a resolution map. As shown, a forward transform A, corresponding to a particular catheter location is first obtained at 810 using, for example, either of the techniques described above.

It will be appreciated that other techniques for determining a resolution map having values indicative of the degree of spatial resolution of the determined physiological information for at least some locations at the endocardium surface can be used.

Once generated, the resolution map may be displayed at 830 to the physician to aid in determining the accuracy and reliability of the reconstructed physiological information. In preferred embodiments the resolution map is overlaid (i.e., superimposed) with the reconstructed physiological signal on the endocardial representation by one of the following techniques:

1. Grid Lines—The resolution values can be represented on the endocardial representation by controlling the grid line density appearing on the endocardial representation. Thus, in areas of high resolution the grid lines on the endocardial representation will appear dense while in areas of low resolution they will appear coarse. Similarly, the resolution can be displayed by superimposing dots on the endocardial representation. In this case resolution is displayed by controlling dot density, instead of grid line density, such that dot density in high resolution areas will be higher than in areas of low resolution.

2. Transparency—The resolution values can also be represented on the endocardial surface by controlling the transparency of the displayed areas. Thus, areas of high resolution will appear opaque while areas of low resolution will appear increasingly transparent.

3. Brightness—The resolution values can also be represented by controlling the brightness of the displayed areas on the endocardium surface representation. Thus, areas of high resolution will appear bright while those of low resolution will appear increasingly dark.

In some embodiments instead of assigning overlaying the resolution value a thresholding scheme may be used. A minimum resolution threshold (for example 1 cm) may be defined. Areas where the resolution is better than the threshold will be displayed (e.g. opaque, bright, etc.) with corresponding physiological information while areas of low resolution will be masked (e.g. transparent, dark, etc.).

In yet other embodiments the resolution may be displayed on an independent endocardial representation, alongside an additional endocardial representation depicting the physiological information.

The physician may use this resolution map to determine the reliability with which data is reconstructed on the endocardium surface representation. If an inadequate resolution is available at a point of interest, the physician may advance the catheter towards the point of interest to improve reconstruction resolution.

Additionally, in some embodiments generated resolution maps are used to construct a composite set of reconstructed physiological information. In particular, in circumstances where for each location of the catheter a separate reconstructed set of physiological information (which may have been obtained over multiple heart beats and/or multiple locations) is available, a corresponding resolution map, for each of those available reconstructed sets, is generated using, for example, one of the techniques described above. Subsequently, a resultant composite set of reconstructed physiological information is generated by selecting, for a particular surface element at the endocardium surface representation, a reconstructed value from that set of reconstruction physiological information whose corresponding resolution map value is the best or most optimal or by performing a weighted average as described above.

B. Isopotential Representation

The reconstructed potentials provide a snapshot of potential distribution on the endocardium surface at a given instant. Such potential values may be color coded and superimposed on the endocardial representation for display. For clarity, contoured isopotential lines may also be added showing lines of interpolated equal potential.

The propagation of potentials (i.e., their temporal behavior) may also be calculated using multiple time instances and displayed in a similar manner. As a result color data and/or isopotential lines will be displayed as an animation depicting the temporal behavior of potential distribution.

C. Timing Map

Timing maps display information pertaining to the timing of particular events relative to the occurrence of other easily detectable reference events. This information may include temporal features such as the onset of depolarization (activation), repolarization and activation duration. Reference events may include the R wave on an ECG or activation time in a specific intracardiac electrogram (e.g. electrode at coronary sinus). One type of timing map, activation time map (isochrone), is commonly used to describe activation wavefront propagation. In this type of map the activation time of each point on the endocardium is determined and its value color coded and displayed on the endocardial surface. In other words, an isochrones map identifies the time instances at which particular locations on the endocardium surface experienced a depolarization of their potentials. The electrical activity during a heart beat cycle (or more) can thus be displayed on a single isochrones contour map showing lines of interpolated equal activation times. The construction of the isochrones map requires the detection of activation instants from reconstructed potentials.

Figure 10:
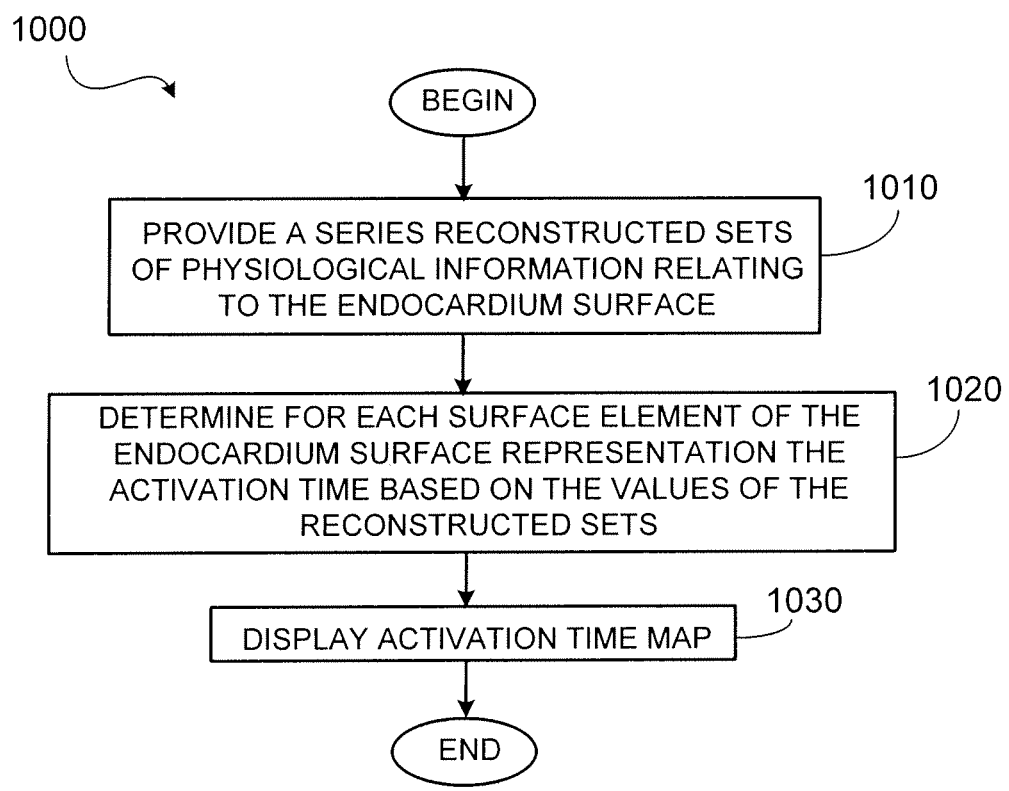
FIG. 10 is a flowchart of an exemplary embodiment of a procedure to generate an activation time map.

FIG. 10 is a flowchart of an exemplary embodiment of a procedure 1000 to generate an activation time map. As shown, multiple reconstructed sets of potential values relating to the endocardium surface are provided at 1010.

Next, for each surface element associated with the series of reconstructed sets, the activation time (i.e., the time at which the potential was depolarized) at that surface element is determined at 1020 based on the values of reconstructed sets. In some embodiments, the activation time is determined by identifying the reconstructed set at which the rate of potential change was the highest. In some other embodiments, the activation time is determined by identifying the first reconstructed set at which there was a potential change, as compared to the preceding reconstructed set, exceeding some pre-determined threshold. In yet other embodiments, activation time is determined using cross-correlation with a template beat in the manner described above. Other ways for establishing the activation time instance can be used. The identified reconstructed set is associated with a particular time instance, which is recorded in the activation time map. It will be appreciated that the entries of the activation time map may have initially been set to a value that is indicative of no associated activation time (e.g., a value of 0 or a negative value).

Once the activation time (if any) has been determined for all the surface elements of the endocardium surface representation, the derived activation time map is displayed at 1030.

While isochrones maps are helpful in depicting activation propagation in a single image, they can be limited in that they discard information related to potential waveforms, amplitude and areas where multiple activations per beat are present.

Additional processing may be conducted to highlight properties of the activation propagation. For example, areas that have not been activated or that experienced more than one activation in a given heart beat may be highlighted for further investigation.

It will be appreciated that activation time maps may be generated for other types of physiological information.

D. Voltage Map

Voltage maps can be used to display characteristics of voltage amplitude in given areas of the endocardium surface. The voltage maps are calculated from the reconstructed potentials over a single or multiple beats. Useful information may be maximum amplitude, or root mean square potential value. Voltage maps are particularly useful for the detection of infracted areas which tend to have lower amplitudes generally <1 mV.

Figure 11:
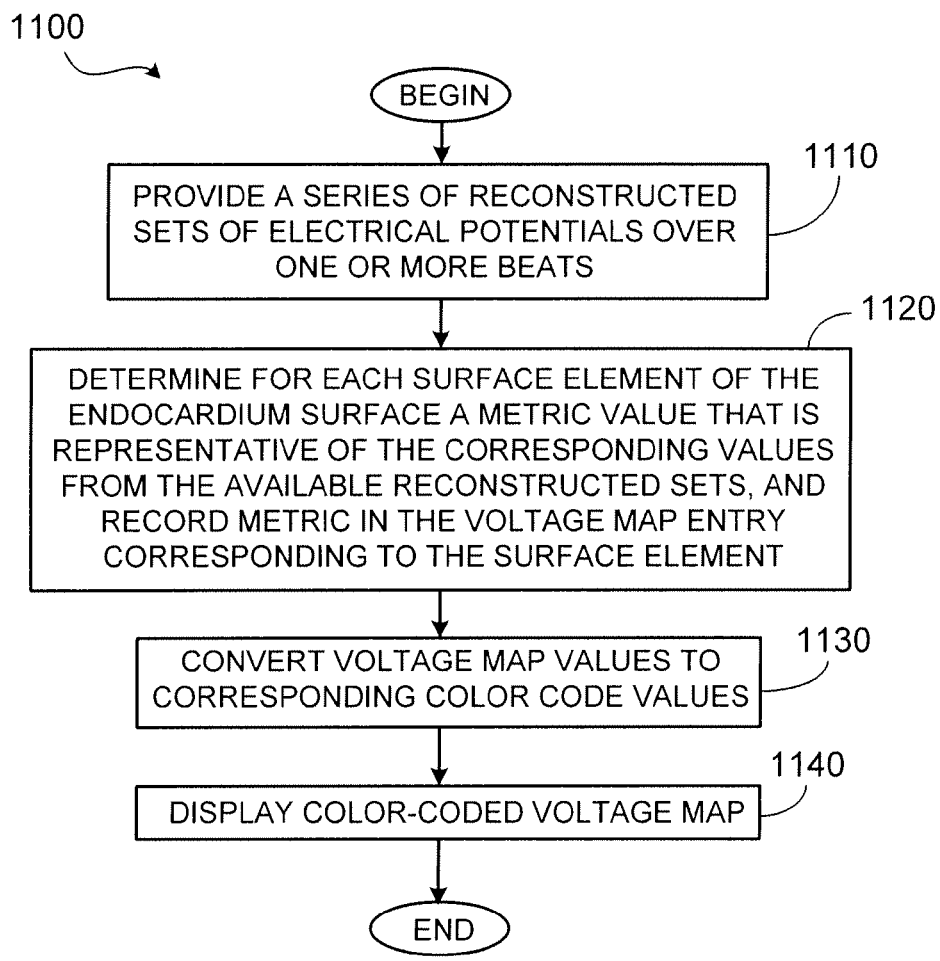
FIG. 11 is a flowchart of an embodiment of an exemplary embodiment of a procedure to generate a voltage map.

FIG. 11 is a flowchart of an embodiment of an exemplary embodiment of a procedure 1100 to generate a voltage map. As shown, one or more reconstructed sets of electrical potentials are provided at 1110. The reconstructed set(s) may correspond to reconstructed potentials computed from a single measurement performed by the multiple electrodes of the catheter 110, or alternatively may correspond to several measurements taken over several heart beats, or may more generally correspond to multiple measurements taken at multiple locations in the heart chamber over several heart beats and/or at different phases of the heart cycle.

The reconstructed sets provided are then processed to determine, for each surface element of the endocardium surface representation, a metric value that is representative of the corresponding values from the reconstructed sets (at 1120). In some embodiments, the metric value is the maximum amplitude potential value identified from the respective values (provided by the available reconstructed sets) associated with a surface element. In some embodiments, the metric value is computed as the root mean square of the various respective values from the reconstructed sets. Other representative values of the potential at various locations of the endocardium surface may be computed. Once the metric value for a particular surface element of the endocardium surface representation has been computed, that value is recorded in the corresponding entry of the voltage map.

Voltage maps may have a large dynamic range of values. While healthy areas of the heart tend to have potential values in the range of 5-60 mV at the endocardium surface, infracted areas tend to have maximum amplitudes lower than 1 mV. This wide dynamic range makes it difficult to visualize these voltages effectively. To enhance visualization, the color map which assigns colors to voltages may be adjusted. One commonly used adjustment is to define a range of interest such that values that lie outside the range are clamped to either minimum or maximum range value. Values in the range are linearly matched to a color map.

Thus, in some embodiments the metric values of the voltage map are converted to corresponding color map values (at 1130). The voltage map containing the color values computed at 1130 is subsequently displayed at 1140 on the endocardium surface representation.

Figure 5:
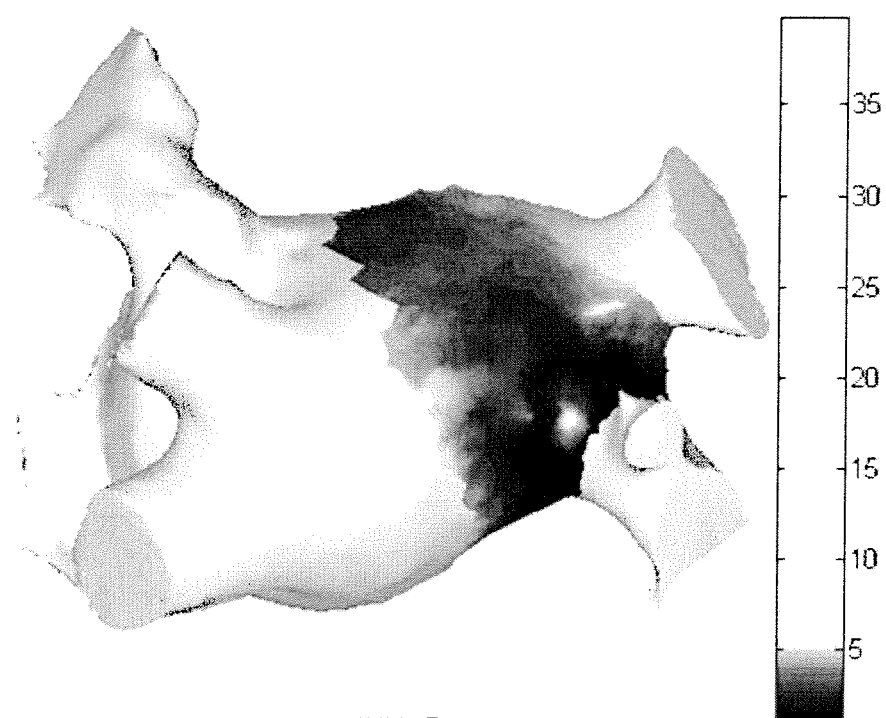
FIG. 5 is an illustration of an exemplary voltage map generated using a linear color map matching scheme.

FIG. 5 is an illustration of an exemplary voltage map generated using a linear color map matching scheme. As shown, areas of differing electrical activity in the endocardium surface are readily discernable. Another useful color conversion scheme for the voltage map procedure 1100 is a logarithmic color conversion scheme.

E. Difference Map

As previously described, another type of post-processing operation that is based on voltage maps is the generation of a difference map. The difference map provides information regarding the effectiveness of the clinical procedure, such as an ablation procedure, performed on a patient to ameliorate the symptoms of arrhythmias. The difference map compares the electrical behavior of the heart, as reflected from two or more voltage maps generated before and after the performance of the particular clinical procedure.

Thus, after generating a first a voltage map, the clinical procedure, for example, an ablation procedure, is performed at the areas of the heart that are determined, aided by the information provided by the first voltage map, to require treatment. After the ablation procedure had been performed, a second voltage map is generated. The values of the first ablation map are subtracted from the corresponding values of the second voltage map. If there is no significant difference between any the respective voltage map entries corresponding to a particular endocardium surface locations where the ablation procedure was performed, this may be indicative that the ablation procedure performed at those locations had little clinical effect.

It will again be appreciated that maps analogous to the voltage maps described above may be generated for other types of physiological information. For example, the difference map could show differences in measured potential at a specific phase in the heart cycle.

F. Frequency Maps

As the understanding of fibrillation mechanisms develops, there is an increased emphasis on using spectral analysis to guide treatment. Spectral analysis and frequency mapping are used to identify localized sites of high-frequency activity during fibrillation. Ablation at these sites results in changes and sometimes termination of the fibrillation, indicating their role in the maintenance of arrhythmia.

In spectral analysis frequency data is color coded and displayed on the 3D anatomical endocardium surface representation. In some embodiments the data displayed is the dominant frequency at which activation takes place in a given location.

Figure 9:
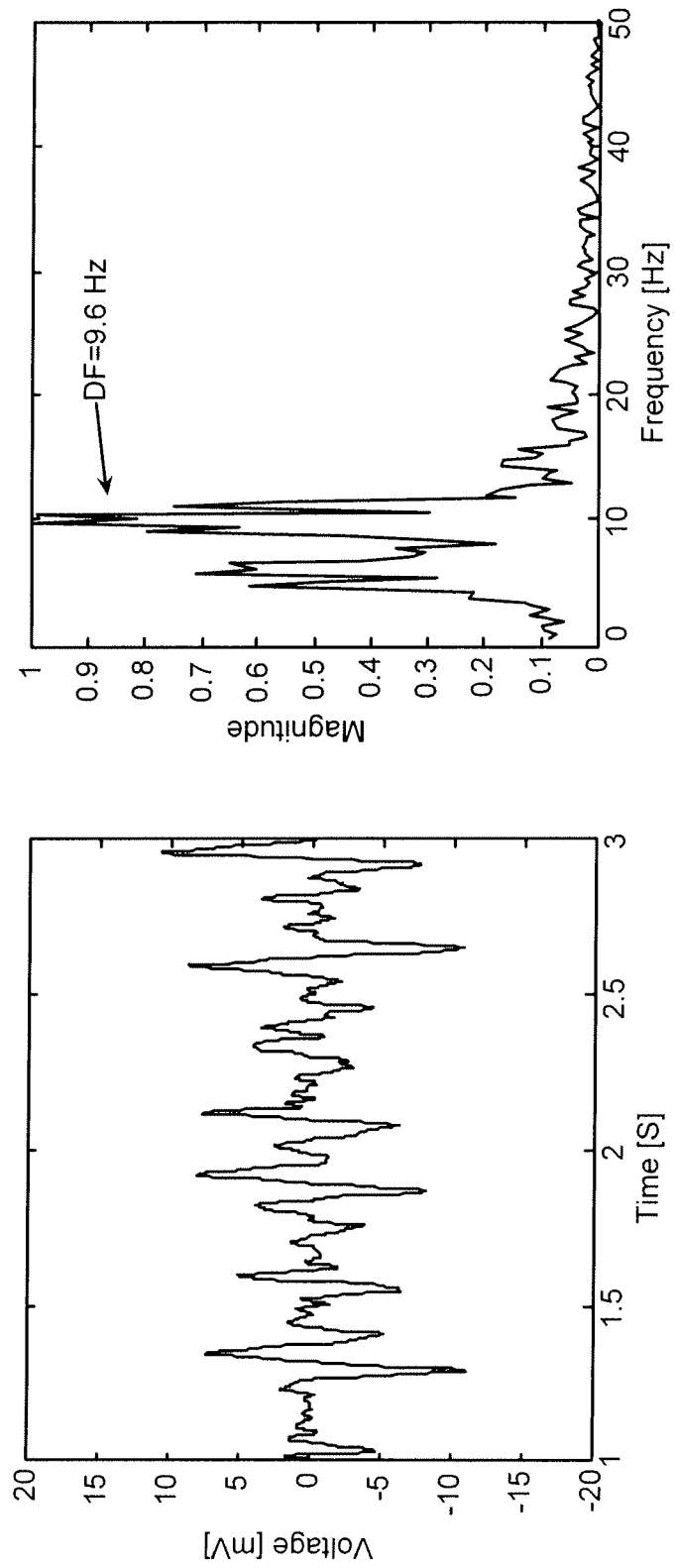
FIG. 9 is a diagram showing a time and frequency representations of an exemplary electrogram.

For example, FIG. 9 is a diagram showing a time and frequency representations of an electrogram. As shown, the image on the left depicts the electrogram potential as a function of time in fibrillating tissue. The image on the right depicts a Fast Fourier Transform (FFT) of the same signal. In this example, the dominant frequency (DF) of the signal is 9.6 Hz. For each location of interest the DF can be calculated by applying an FFT on the time-dependent signal, determining the frequency at which maximum amplitude is present. The DF is then color coded and displayed on corresponding chamber anatomy.

Figure 13:
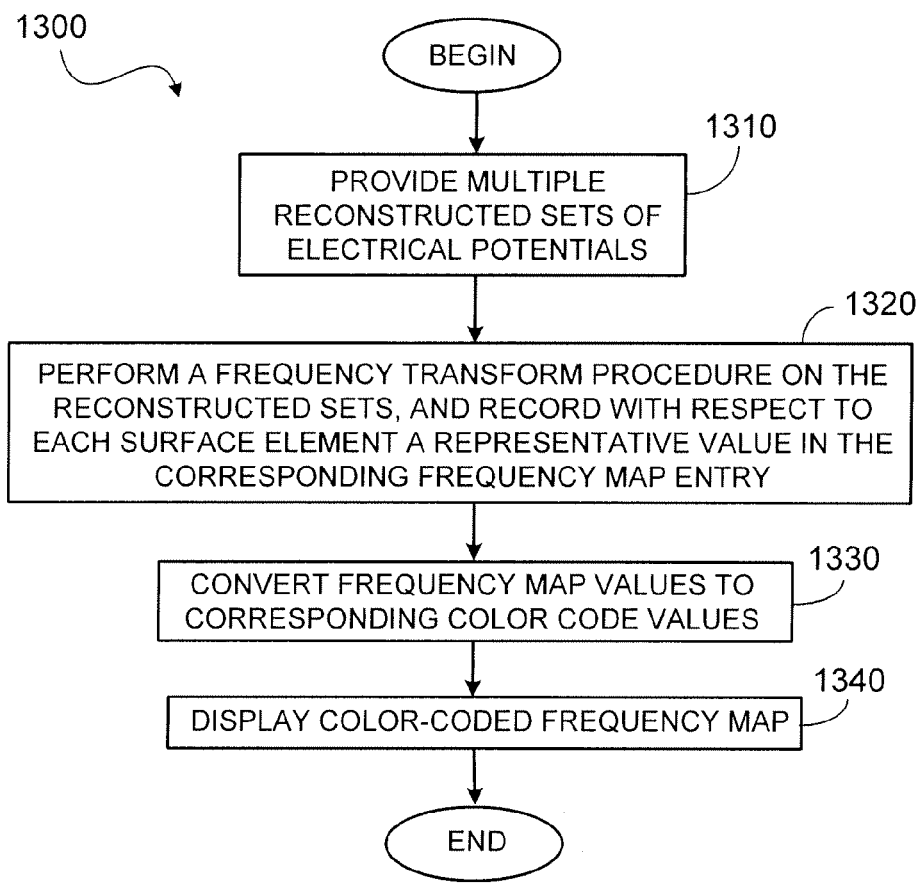
FIG. 13 is a flowchart of an exemplary embodiment of a procedure for generating a frequency map.

Similar spectral analysis may thus be performed with respect to other reconstructed sets of the endocardium surface. FIG. 13 is a flowchart of an exemplary embodiment of a procedure 1300 for generating a frequency map. As shown, multiple reconstructed sets of physiological information at the endocardium surface are provided at 1310. The reconstructed sets correspond to a temporal sequence of measurements performed by the catheter 110. Subsequently, a frequency transform procedure, such as a Fast Fourier Transform, is performed on the reconstructed sets at 1320. The frequency transform procedure is performed individually for the values of the reconstructed sets corresponding to individual surface elements of the endocardium surface representation. A representative value, for example a dominant frequency, obtained from the resultant frequency representation of the time behavior for a particular surface element is recorded in the frequency map entry corresponding to that particular surface element. In some embodiments, the temporal data with respect to which the frequency transform is performed could correspond to multiple surface elements.

Once the frequency transform procedure has been completed, the frequency representation values are converted to corresponding color map values to enable the resultant values to be more easily observed when displayed (at 1330). The color frequency map, containing the color values computed at 1330, is subsequently displayed at 1340 on the endocardium surface representation.

Applications

Mapping of electro-anatomical characteristics of heart tissue can be helpful in guiding therapies for a number of diseases including arrhythmia and heart failure.

For targeted therapy of arrhythmia, it is necessary to accurately identify the source of the arrhythmia. The source of the arrhythmia may be identified by electro-anatomically characterizing the underlying tissue during sinus rhythm, spontaneous or induced arrhythmia, or during pacing. Electro-anatomical characterization includes a number of spatio-temporal features of the conduction. For example, these include activation time mapping to identify early activation sites that are indicative of exit sites and unwanted automatic cell firing, maximum voltage to identify low voltage areas that are indicative of infracted regions, as well as repolarization time and spectral behavior. Once the source of the arrhythmia has been identified, a therapeutic course of action is undertaken. Therapy may include ablation of tissue accomplished by the delivery of RF energy, microwave energy, cooling, ultrasound, chemical agents, radiation or laser. Alternatively, therapy may also be accomplished by the introduction and targeted delivery of biological agents such as cells capable of performing myocardial repair, or genes capable of changing physiological behavior.

For cell therapy, see, for example: Ronglih Liao, Ph.D., "Cell Therapy Attenuates Deleterious Ventricular Remodeling and Improves Cardiac Performance After Myocardial Infarction", *Circulation* (Apr. 10, 2001); Pieter C. Smits, "Catheter-Based Intramyocardial Injection of Autologous Skeletal Myoblasts as a Primary Treatment of Ischemic Heart Failure", *Journal of the American College of Cardiology*, Vol. 42, No. 12 (2003); Gepstien, "Regenerating the Heart Using Human Embryonic Stem Cells—from Cell to Bedside", *IMAJ*, Vol 8 (March 2006).

For gene therapy, see, for example: J. Kevin Donahue, "Focal modification of electrical conduction in the heart by viral gene transfer", *Nature Medicine*, Volume 6, Number 12 (December 2000); and Kevin Donahue, M. D., "Targeted Modification of Atrial Electrophysiology by Homogeneous Transmural Atrial Gene Transfer", *Circulation* (Jan. 25, 2005).

In patients with heart failure, electro-anatomical mapping primarily involves the identification of areas with low potentials that are indicative of infarction as well as areas that exhibit reduced mechanical motion. Once diseased areas have been identified, therapy may involve the targeted delivery of introduction of cells or genes capable of performing myocardial repair and regeneration. Recent advances in the area of stem cell biology have provided scientists with potential tools to develop novel strategies for myocardial regeneration. Such biological therapies also affect the electrical properties of the tissue which can be mapped using electro-anatomical mapping.

For both arrhythmia and heart failure treatment, following therapy delivery, electro-anatomical mapping may be used to validate therapy effectiveness. For example, this may be accomplished during the same procedure to validate conduction block in areas where ablation energy was delivered or to validate the regenerated mechanical motion following biological implantation. Alternatively, or in addition, a scheduled follow up may be performed several months after the procedure to validate long term therapy effectiveness.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   inserting a catheter into a heart cavity having an endocardium surface, the catheter comprising multiple, spatially distributed electrodes;
   moving the catheter to each of multiple, different positions in the heart cavity;
   for each of the different catheter positions, determining the positions of the catheter electrodes with respect to the endocardium surface;

for each of the different catheter positions, measuring signals at the catheter electrodes in response to electrical activity in the heart cavity;

determining physiological information at multiple locations of the endocardium surface based on the determined positions of the catheter electrodes and the measured signals at the different catheter positions by applying a transformation function to the measured signals, the transformation function relating the measured signals from at least some of the different positions to the physiological information at the multiple locations of the endocardium surface and being based in part on the catheter's location relative to the endocardium surface; and displaying information related to at least some of the determined physiological information.

2. The method of claim 1, wherein:
determining the physiological information comprises determining electrical potential values at the multiple locations of endocardium surface at each of one or more different phases of the heart beat cycle, and
displaying the information related to at least some of the determined physiological information comprises displaying electrical potential values at the multiple locations of endocardium surface at each of one or more different phases of the heart beat cycle.

3. The method of claim 1, wherein:
determining the physiological information comprises determining a maximum voltage amplitude for one or more heart beat cycles at different ones of the endocardium surface locations; and
displaying the information related to at least some of the determined physiological information comprises displaying information related to the maximum voltage amplitude at different ones of the endocardium surface locations.

4. The method of claim 1, wherein:
determining the physiological information comprises determining a maximum voltage amplitude for one or more heart beat cycles at different ones of the endocardium surface locations; and
displaying the information related to at least some of the determined physiological information comprises displaying information related to the maximum voltage amplitude at different ones of the endocardium surface locations.

5. The method of claim 1, wherein:
determining the physiological information comprises determining a frequency representation of electrical activity at multiple locations of the endocardium surface during the heart beat cycle, wherein the frequency representation is computed based on electrical potential values at the multiple locations of endocardium surface at different phases of the heart beat cycle; and
displaying the information related to at least some of the determined physiological information comprises displaying information related to the determined frequency representation.

6. The method of claim 1, wherein:
determining the physiological information comprises determining an activation time for each of different locations of the endocardium surface; and
displaying the information related to at least some of the determined physiological information comprises displaying information related to the determined activation time for each of different locations of the endocardium surface.

7. The method of claim 1, wherein the measured signals are synchronized based on physiological data including at least one of: ECG and intracardiac electrograms.

8. The method of claim 1, wherein the determination of the physiological information at the multiple locations of the endocardium surface further comprises determining the transformation function by calculating a forward transformation for relating the physiological information at the multiple locations of the endocardium surface to the signals measured for the different positions of the catheter in the heart cavity and inverting the forward transformation.

9. The method of claim 8, wherein the inverting comprises reformulating an underdetermined matrix inversion by regularization.

10. The method of claim 9, wherein the inverting further comprises a least squares minimization.

11. The method of claim 1, wherein determining the position of the catheter electrodes with respect to the endocardium surface comprises using at least one of electric fields, magnetic fields, fluoroscopy, and ultrasound to determine a position of the catheter in a first coordinate system.

12. The method of claim 1, wherein determining the position of the catheter with respect to the endocardium surface further comprises registering a representation of the endocardium surface, the representation having been obtained prior to inserting the catheter into the heart cavity, with the first coordinate system.

13. The method of claim 1, wherein determining the position of the catheter electrodes comprises measuring information about at least one of a position and orientation of the catheter within the heart cavity.

14. The method claim 13, wherein:
determining the position of the catheter electrodes is based further on information about the distribution of the electrodes on the catheter; and
measuring information about at least one of a position and orientation of the catheter within the heart cavity comprises measuring the position of one or more catheter electrodes within the heart cavity.

15. The method of claim 1, wherein determining the position of the catheter electrodes comprises directly measuring the position of each catheter electrode within the heart cavity.

16. The method of claim 1, further comprising using the determined physiological information to guide ablation of one or more selected regions of the heart.

17. The method of claim 16, further comprising repeating the measurement of catheter electrode signals and the determination of the physiological information after the ablation treatment, and displaying a difference map comprising information about how the determined physiological information changed in response to the ablation treatment.

18. The method of claim 1, further comprising using the determined physiological information to guide cell therapy, gene therapy, or application of other biological agents.

19. The method of claim 1, wherein the signals are measured during multiple electrical heart beat cycles and wherein the physiological information is determined, at least in part, by combining information derived from the signals for different heart beat cycles.

20. The method of claim 1, wherein the device to determine the position of the catheter electrodes with respect to the endocardium surface comprises a device configured to measure information about at least one of a position and orientation of the catheter within the heart cavity.

21. A system comprising:
a catheter configured to be inserted into a heart cavity having an endocardium surface and to move to each of multiple positions in the heart cavity, the catheter comprising:
multiple, spatially distributed electrodes, the multiple electrodes configured to measure signals in response to electrical activity in the heart cavity;
a device configured to determine, for each of the different catheter positions, the positions of the catheter electrodes with respect to the endocardium surface;
a processing unit configured to determine physiological information at multiple locations of the endocardium surface based on the determined positions of the catheter electrodes and the measured signals at the different catheter positions by applying a transformation function to the measured signals, the transformation function relating signals measured from at least some of the different positions to the physiological information at the multiple locations of the endocardium surface and being based in part on the catheter's location relative to the endocardium surface; and
a display device configured to display at least a portion of the endocardium surface to include at least some information related to the determined physiological information.

22. The system of claim 21, wherein the processing unit is further configured to determine the transformation function by calculating a forward transformation for relating the physiological information at the multiple locations of the endocardium surface to the signals measured for the different positions of the catheter in the heart cavity and inverting the forward transformation.

23. The system of claim 21, wherein:
the configurations to cause the processing device to determine the physiological information comprises configurations to determine electrical potential values at the multiple locations of endocardium surface at each of one or more different phases of the heart beat cycle, and
the configurations to display the information related to at least some of the determined physiological information comprise configurations to display electrical potential values at the multiple locations of endocardium surface at each of one or more different phases of the heart beat cycle.

24. The system of claim 21, wherein:
the configurations to determine the physiological information comprise configurations to determine a maximum voltage amplitude for one or more heart beat cycles at different ones of the endocardium surface locations; and
the display device is configured to display the information related to at least some of the determined physiological information including displaying information related to the maximum voltage amplitude at different ones of the endocardium surface locations.

25. The system of claim 21, wherein:
the configurations to determine the physiological information comprise configurations to determine a maximum voltage amplitude for one or more heart beat cycles at different ones of the endocardium surface locations; and
the display device is configured to display the information related to at least some of the determined physiological information including displaying information related to the maximum voltage amplitude at different ones of the endocardium surface locations.

26. The system of claim 21, wherein:
the configurations to determine the physiological information comprise configurations to determine a frequency representation of electrical activity at multiple locations of the endocardium surface during the heart beat cycle, wherein the frequency representation is computed based on electrical potential values at the multiple locations of endocardium surface at different phases of the heart beat cycle; and
the display device is configured to display the information related to at least some of the determined physiological information including displaying information related to the determined frequency representation.

27. The system of claim 21, wherein:
the configurations to determine the physiological information comprise configurations to determine an activation time for each of different locations of the endocardium surface; and
the display device is configured to display the information related to at least some of the determined physiological information including displaying information related to the determined activation time for each of different locations of the endocardium surface.

28. The system of claim 21, wherein the processor is further configured to synchronize the measured signals based on physiological data including at least one of: ECG and intracardiac electro grams.

29. The system of claim 21, wherein the configurations to cause the processing unit to determine the physiological information at the multiple locations of the endocardium surface further comprises configurations to determine the transformation function by calculating a forward transformation for relating the physiological information at the multiple locations of the endocardium surface to the signals measured for the different positions of the catheter in the heart cavity and inverting the forward transformation.

30. The system of claim 21, wherein the device to determine the position of the catheter electrodes with respect to the endocardium surface comprises a device configured to determine the location using at least one of electric fields, magnetic fields, fluoroscopy, and ultrasound to determine a position of the catheter in a first coordinate system.

31. The system of claim 21, wherein the device to determine the position of the catheter electrodes with respect to the endocardium surface comprises a device configured to register a representation of the endocardium surface, the representation having been obtained prior to inserting the catheter into the heart cavity, with the first coordinate system.

32. The system of claim 21, wherein the device to determine the position of the catheter electrodes with respect to the endocardium surface comprises a device configured to measure the position of each catheter electrode within the heart cavity.

33. The system of claim 21, wherein the processing unit is configured to determine the physiological information, at least in part, by combining information derived from the signals for different heart beat cycles.

* * * * *